US008790614B2

(12) United States Patent  
Richards et al.

(10) Patent No.: US 8,790,614 B2  
(45) Date of Patent: Jul. 29, 2014

(54) ZNO STRUCTURES AND METHODS OF USE

(75) Inventors: Ryan M. Richards, Golden, CO (US); Lifang Chen, Shanghai (CN); Juncheng Hu, Wuhan (CN)

(73) Assignee: Colorado School of Mines, Golden, CO (US)

( * ) Notice: Subject to any disclaimer, the term of this patent is extended or adjusted under 35 U.S.C. 154(b) by 0 days.

(21) Appl. No.: 12/685,465

(22) Filed: Jan. 11, 2010

(65) Prior Publication Data

US 2010/0284893 A1 Nov. 11, 2010

Related U.S. Application Data

(60) Provisional application No. 61/143,489, filed on Jan. 9, 2009.

(51) Int. Cl.
*C01G 9/02* (2006.01)
*C01B 31/20* (2006.01)
*C07C 29/159* (2006.01)

(52) U.S. Cl.
USPC ............ 423/622; 423/418.2; 423/648.1; 518/726

(58) Field of Classification Search
USPC ............ 423/622, 418.2, 648.1; 518/726
See application file for complete search history.

(56) References Cited

U.S. PATENT DOCUMENTS

| 1,558,559 | A | 10/1925 | Mittasch et al. |
| 1,569,755 | A | 1/1926 | Irvin |
| 7,491,423 | B1 | 2/2009 | Hsu et al. |
| 2004/0105810 | A1* | 6/2004 | Ren et al. ............... 423/624 |
| 2007/0140951 | A1 | 6/2007 | O'Brien et al. |
| 2008/0107876 | A1 | 5/2008 | Yi et al. |
| 2008/0280058 | A1 | 11/2008 | Krunks et al. |
| 2009/0297626 | A1 | 12/2009 | O'Brien et al. |

FOREIGN PATENT DOCUMENTS

WO WO 2007/093415 8/2007
WO WO 2009/097627 8/2009

OTHER PUBLICATIONS

Al-Assiri, et al., "Synthesis and characterisation of ZnO structures containing the nanoscale regime" May 2009, International J. of Nano and Biomaterials, 2(1), pp. 255-262.*
Chiang et al., "Ion sensitivity of the flowerlike ZnO nanorods synthesized by the hydrothermal process" May 27, 2009, J. Vac. Sci. Technol. B 27(3), pp. 1462-1465.*
Aida et al. (Mar. 1, 2009) "Nanocrystalline ZnO Thin Film Growth by Ultrasonic Spray frm a Non-Aqueous Solution," *Proc. Inst. Mech. Eng. N, J. Nanoeng. Nanosyst.* 223(1):25-33.
Andelman et al. (2007) "Diameter Control and Photoluminescence of ZnO Nanorods from Trialkymines" *Jour. Nanomater.* 2007:73824.
Andelman et al (2005) "Morphological Control and Photoluminescence of Zinc Oxide Nanocrystals" *J. Phys. Chem. B* 109:14314-14318.
Badlani et al. (2001) "Methanol: A 'Smart' Chemical Probe Molecule," *Catal. Lett.* 75(3-4):137-149.
Belcher et al. (May 2, 1996) "Control of Crystal Phase Switching and Orientation by Soluble Mollusc-Shell Proteins," *Nature* 381:56-58.
Bolis et al. (1989) Effect of Form on the Surface Reactivity of Differently Prepared Zinc Oxides, *J. Chem. Soc., Faraday Trans.* 85(4):855-867.
Changsong et al. (Dec. 2007) "Micro Structural Evolution of Well-Aligned ZnO Nanorods Array Films in Aqueous Solution" *J. Wuhan Univ. Technology-mater. Sci. Ed.* 22(4):603-606.
Cheng (Mar. 2004) "Hydrothermal Synthesis of One-Dimensional ZnO Nanostructures with Different Aspect Ratios" *Chem Commun.* 986-987.
Cheng (2006) "Fine-Tuning the Synthesis of ZnO Nanostructures by an Alcohol Thermal Process" *J. Phys. Chem. B* 110:10348-10353.
Chiang et al. (May 27, 2009) "Ion Sensitivity of the Flowerlike ZnO Nanorods Synthesized by the Hydrothermal Process," *J. Vac. Sci. Technol. B.* 27(3):1462-1465.
Cho et al. (Web Release Jul. 25, 2008) "Morphology Controlled Growth of ZnO Nanostructures using Microwave Irradiation: from Basic to Complex Structures" *J. Phys. Chem. C.* 112(33):12769-12776.
Cozzoli et al. (2003) "ZnO Nanocrystals by a Non-Hydrolic Route: Synthesis and Characterization" *J. Phys. Chem. B* 107:4756-4762.
Dai et al. (Sep. 2001) "Layer-by-Layer Self-Assembly of Polyelectrolyte and Low Molecular Weight Species into Capsules," *Adv. Mater.* 13(17):1339-1342.
Diao et al. (Web Release Dec. 21, 2001) "Hydrolysis of Magnesium Methoxide. Effects of Toluene on Gel Structure and Gel Chemistry," *Chem. Mater.* 14(1):362-368.
Ding et al. (2004) "Structure Analysis of Nanowires and Nanobelts by Transmission Electron Microscopy" *J. Phys. Chem. B.* 108:12280-12291.
Eckert et al. (Sep. 26, 1996) "Supercritical Fluids as Solvents for Chemical and Materials Processing," *Nature* 383:313-318.
Falini et al. (1996) "Control of Aragonite or Calcite Polymorphism by Mollusk Shell Macromolecules," *Science* 271:67-69.

(Continued)

*Primary Examiner* — Steven Bos

(74) *Attorney, Agent, or Firm* — Lathrop & Gage LLP

(57) ABSTRACT

ZnO structures comprising crystalline ZnO micro or nanorods and methods for making and using these ZnO structures are provided. The side surface of the central portion of each rod may comprise planes of the form $\{1\ 0\ -1\ 0\}$, $\{0\ 1\ -1\ 0\}$, $\{-1\ 1\ 0\ 0\}$, $\{-1\ 0\ 1\ 0\}$, $\{0\ -1\ 1\ 0\}$ or $\{1\ -1\ 0\ 0\}$, with central edge regions including a crystallographic plane of the form $\{2\ -1\ -1\ 0\}$ or $\{-2\ 1\ 1\ 0\}$. The tip of the rod may comprise planes of the form $\{1\ 0\ -1\ 1\}$ $\{0\ 1\ -1\ 1\}$, $\{-1\ 1\ 0\ 1\}$, $\{-1\ 0\ 1\ 1\}$, $\{0\ -1\ 1\ 1\}$ or $\{1\ -1\ 0\ 1\}$ with tip edge regions including a crystallographic plane of the form $\{2\ -1\ -1\ 2\}$ or $\{-2\ 1\ 1\ 2\}$. The rods may be joined at or near their bases to form a "flower-like" morphology. In an embodiment, a synthesis mixture is prepared by dissolving a zinc salt in an alcohol solvent, followed by addition of at least two additives. The zinc salt may be zinc nitrate hexahydrate, the first additive may be benzyl alcohol and the second additive may be urea.

22 Claims, 18 Drawing Sheets

(56) References Cited

OTHER PUBLICATIONS

Fulcher et al. (2004) "Production of Zinc Oxide with Variable Morphology by Two Novel Wet-Chemical Methods," $1^{st}$ Year Project in the Electron Microscope Unit at Sydney University 10 pages.

Gao (2003) "Crystallographic Orientation-Alligned ZnO Nanorods Grown by a Tin Catalyst," Nano. Lett. 3(9): 1315-1320.

Gao et al. (2006) "One Dimensional Wurzite Semiconducting Nanostructures," In; Scanning Microscopy for Nanotechnology, Zhou et al. Eds., Springer, New York pp. 384-426.

Gibson (Web Release Oct. 1, 1996) "The Organometallic Chemistry of Carbon Dioxide," Chem. Rev. 96(6):2063-2095.

Greene et al. (Web Release Sep. 11, 2006) "Solution-Grown Zinc Oxide Nanowires," Inorg. Chem. 45:7535-7543.

Hu et al. (Web Release Jul. 20, 2007) "MgO(111) Nanosheets with Unusual Surface Activity," J. Phys. Chem. C 111(32):12038-12044.

Hu et al. (Jan. 2008) "Preparation and Surface Activity of Single-Crystalline NiO(111) Nanosheets with Hexagonal Holes: A Semiconductor Nanospanner," Adv. Mater 20(2):267-271.

Huang et al. (Jan. 2001) "Catalytic Growth of Zinc Oxide Nanowires by Vapor Transport," Adv. Mater. 13(2):113-116.

Huang et al. (2001) "Room Temperature Ultraviolet Nanowire Nanolasers," Science 292:1897-1899.

Ischenko et al. (1945) "Zinc Oxide Nanoparticles with Defects," Adv. Funct. Mater. 15:1945-1954.

Jessop et al. (Mar. 17, 1994) "Homogenous Catalytic Hydrogenation of Supercritical Carbon Dioxide," Nature 368:231-233.

Jessop et al. (Mar. 1995) "Homogeneous Hydrogenation of Carbon Dioxide," Chem. Rev. 95(2):259-272.

Jessop et al. (2004) "Recent Advances in the Homogenous Hydrogenation of Carbon Dioxide," Coord. Chem. Rev. 248:2425-2442.

Jingfa et al. (Apr. 1, 1997) "A Novel Process for the Preparation of Cu/ZnO and Cu/ZnO/$Al_2O_3$ Ultrafine Catalysts: Structure, Surface Properties, and Activity for Methanol Synthesis from $CO_2+H_2$," J. Catal. 167(1):92-165.

Jones et al. (Web Release May 5, 2004) "Photoelectron Spectroscopic and Electronic Structure Studies of $CH_2O$ Bonding and Reactivity on ZnO Surfaces: Steps into the Methanol Synthesis Reaction," Inorg. Chem. 43(11):3349-3370.

Kim et al. (Web Release Sep. 30, 2008) "COntinous Synthesis of Surface-Modified Metal Oxide Nanoparticles Using Supercritical Methanol for Highly Stabilized Nanofluids," Chem. Mater. 20:6301-6303.

Kisailus et al. (2006) "Kinetically Controlled Catalytic Formation of Zinc Oxide Thin Films at Low Temperature" J. Am. Chem. Soc. 128(31): 10276-10280.

Kovacik et al. (Jun. 25, 2007) "F Centers Verses Dimer Vacancies on ZnO Surfaces: Characterization by STM and STS Calculations," Angew. Chem. Int. Ed. 46(26):4894-4897.

Leitner, W. (Nov. 3, 1995) "Carbon Dioxide as a Raw Material: The Synthesis of Fromic Acid and its Derivatives from $CO_2$," Angew. Chem. Int. Ed. 34(20):2207-2221.

Li et al. (Oct. 4, 2004) "Single-Crystal Hexagonal Disks and Rings of ZnO: Low-Temperature, Large-Scale Synthesis and Growth Mechanism," Angew. Chem. Int. Ed. 2004 43(39):5238-5242.

Lindsay et al. (Web Release May 15, 2002) "Impact of Defects on the Surface Chemistry of ZnO(000(1)over-bar)-O," J. Am. Chem. Soc. 124 (24):7117-712.

Liu et al. (2003) "Hydrothermal Synthesis of ZnO Nanorods in the Diameter Regime of 50 nm" J. Am. Chem. Soc. 125: 4430-4431.

Munshi et al. (Web Release Jun. 13, 2002) "Hydrogenation of Carbon Dioxide Catalyzed by Ruthenium Trimethylphosphine Complexes: The Accelerating Effect of Certain Alcohols and Amines," J. Am. Chem. Soc. 124(27):7963-7971.

Natile et al. (Web Release May 25, 2005) "$CoO_x/CeO_2$ Nanocomposite Powders Synthesis, Characterization and Reactivity," Chem. Mater. 17(13):3403-3414.

Natile et al. (Web Release Jun. 6, 2006) "$WO_3/CeO_2$ Nanocomposite Powders: Synthesis, Characterization, and Reactivity," Chem. Mater. 18(14):3270-3280.

Niederberger et al. (Web Release Sep. 27, 2002) "Benzyl Alcohol and Titanium Tetrachloride—A Versatile Reaction System for the Nonaqueous and Low-Temperature Preparation of Crystalline and Luminescent Titania Nanoparticles," Chem. Mate. 14(10):4364-4370.

Niederberger et al. (Web Release Oct. 30, 2002) "Benzyl Alcohol and Transition Metal Chlorides as a Versatile Reaction System for the Nonaqueous and Low-Temperature Synthesis of Crystalline Nano-Objects with Controlled Dimensionality," J. Am. Chem. Soc. 124(46):13642-13643.

Niederberger et al. (Web Release Jun. 29, 2004) "Nonaqueous and Halide-Free Route to Crystalline $BaTiO_3$, $SrTiO_3$, and $(Ba,Sr)Ti)_3$ Nanoparticles via a Mechanism Involving C-C Bond Formation," J. Am. Chem. Soc. 126(29):9120-9126.

Niederberger et al. (Apr. 19, 2004) "A General Soft-Chemistry Route to Perovskites and Related Materials: Synthesis of $BaTiO_3$, $BaZrO_3$, and $LiNbO_3$ Nanoparticles," Angew. Chem. Int. Ed. 43(17):2270-2273.

Niederberger et al. (2007) "Nonaqueous Synthesis, Assembly and Formation Mechanisms of Metal Oxide Nanocrystals," Int. J. Nanotechnol. 4(3):263-281.

Ohara et al. (Web Release Dec. 2007) "Continuous Production of Fine Zinc Oxide Nanorods by Hydrothermal Synthesis in Supercritical Water" J Mater. Sci. 43:2393-2396.

Ohara et al. (2004) "Hydrothermal Synthesis of Fine Zinc Oxide Particles Under Supercritical Conditions" Solid State Ionics 172: 261-264.

Olah, G.A. (Apr. 29, 2005) "Beyond Oil and Gas: The Methanol Economy," Angew. Chem. Int. Ed. 44(18):2636-2639.

Oliveira et al. (2003) "Controlled Precipitation of Zinc Oxide Particles at Room Temperature" Chem Mater. 15:3202-3207.

Omae (Jun. 30, 2006) "Aspects of Carbon Dioxide Utilization," Catal. Today 115(1-4):33-52.

Peiro et al. (Jul. 1, 2005) "Nanostructured Zinc Oxide Films Grown from Microwave Activated Aqueous Solutions" Thin Solid Films 483(1-2): 79-83.

Pinna et al. (Aug. 20, 2004) "Nonaqueous Synthesis of Nanocrystalline Semiconducting Metal Oxides for Gas Sensing," Angew. Chem. 116(33):4445-4449.

Polleux et al. (Dec. 23, 2005) "Template-Free Synthesis and Assembly of Single-Crystalline Tungsten Oxide Nanowires and their Gas-Sensing Properties," Angew. Chem. Int. Ed. 45(2):261-265.

Savu et al. (2009) "The Effect of Cooling Rate During Hydrothermal Synthesis of ZnO Nanorods" J. Cryst. Growth. 311: 4102-4108.

Schilke et al. (May 15, 1999) "In Situ Infrrared Study of Methanol Synthesis from $CO_2/H_2$ on Titania and Zirconia Promoted $Cu/SiO_2$," J. Catal. 184(1):144-156.

Shaikh, S. S. (Web Release May 9, 1996) "Organic Carbonates," Chem. Rev. 96(3):951-976.

Spence J.C.H. (2003) "Oxygen in Crystals—Seeing is Believing," Science 299:839-841.

Srivastava et al. (2009) "Zinc Crystallographically oriented Nanorods and Nanowires of RF-Manetron-Sputtered Zinc Oxide" J. Nanomater. 2009:3103560.

Sun et al. (Web Release Jan. 2009) "Fabrication and Wettability of ZnO Nanorod Array" J. Mater. Sci. Technol. 25(1):53-57.

Tian et al. (Web Release Oct. 9, 2002) "Biomometic Arrays or Oriented Helical ZnO Nanorods and Columns," J. Am. Chem. Soc. 124(44)12954-12955.

Tian et al. (2003) "Complex and Oriented ZnO Nanostructures," Nature Mater. 2:821-826.

Tonto (Web Release Oct. 9, 2006) "Preparation of ZnO Nanorod by Sovothermal Reaction of Zinc Acetate in Various Alcohols" Ceram. Internat. 34: 57-62.

Veriansyah et al. (Feb. 2010) "Continuous Synthesis of Surface-Modified Zinc Oxide Nanoparticles in Supercritical Methanol," J. of Supercritical Fluids 52(1):76-83.

Wang et al. (Jun. 1, 2006) "Synthesis of Well-Aligned ZnO Nanorod Arrays with Hight Optical Property via a Low-Temperature Solution Method," J. Cryst. Growth 291(2):334-349.

Wang et al. (Apr. 22, 2008) "Growth mechanisim and Joint Structure of ZnO Tetrapods," J Phys D: Appl Phys 41:1-6.

(56) References Cited

OTHER PUBLICATIONS

Wang et al. (Apr. 14, 2006) "Piezoelectric Nanogenerators Based on Zinc Oxide Nanowire Arrays," *Science* 312:242-246.

Wang et al. (2004) "Semiconducting and Piezoelectric Oxide Nanostructures Induced by Polar Surfaces" *Adv. Funct. Mater.* 14(10): 943-956.

Wang (2005) "Controllable Synthesis of ZnO Nanocrystals via a Surfactant-Assisted Alcohol Thermal Process at a Low Temperature" *Mat Lett.* 59: 2867-2871.

Wen et al. (Web Release Dec. 13, 2007) "Controllable Growth of ZnO Nanostructures by a Simple Solvothermal Process" *J. Phys. Chem. C.* 112:106-111.

Wu et al. (Feb. 2002) "Low-Temperature Growth of Well-Aligned ZNO Nanorods by Chemical Vapor Deposition," *Adv. Mater.* 14(3):215-218.

Yang et al. (Web Release Jul. 1, 2006) "Controlled Synthesis and Self-Assembly of $CeO_2$ Nanocubes," *J. Am. Chem. Soc.* 128(29):9330-9331.

Yin et al. (1999) "Recent Developments in the Activation of Carbon Dioxide by Metal Complexes," *Coord. Chem. Rev.* 181:27-59.

Yu et al. (Web Release Feb. 2, 2005) "A General Low-Temperature Route for Large-Scale Fabrication of Highly Oriented ZnO Nanorod/Nanotube Arrays," *J. Am. Chem. Soc.* 127(8):2378-2379.

Yu et al. (Web Release Apr. 28, 2007) "Carbon Dioxide Fixation into Chemicals (Methyl Formate) at Hight Yields by Surface Coupling over a Pd/Cu/ZnO Nanocatalyst," *J. Am. Chem. Soc.* 129(20):6360-6361.

Zecchina et al. (Feb. 26, 1996) "IR Studies of CO and NO Adsorbed on Well Characterized Oxide Single Microcrystals," *Catalysis Today* 27(3-4):403-435.

Zhang et al. (2002) "Control of ZnO Morphology via a Simple Solution Route," *Chem Mater.* 14: 4172-4177.

Zhang et al. (Jul. 29, 2006) "Site-Specific Nucleation and Growth Kinetics in Hierarchial Nanosynthesis of Branched ZnO Crystallites," *J. Am. Chem. Soc.* 128(33):10960-10968.

Zhang et al. (Jan. 25, 2008) "Hydrogenation of Carbon Dioxide is Promoted by a Task-Specific Ionic Liquid," *Angew. Chem. Int. Ed.* 47(6):1127-1129.

Zhong et al. "Nonhydrolytic Alcoholysis Route to Morphology-controlled ZnO Nanocrystals," *Small* 3(7) 1194-1199.

Zhu et al. (Nov. 6, 2006) "Efficient Preparation and Catalytic Activity of MgO(111) Nanosheets,"*Angew. Chem. Int. Ed.* 45(43):7277-7281.

Al-Assiri (2009) "Synthesis and Characterisation of ZnO Structures Containing the Nanoscale Regime" *Int. J. Nano and Biomat.* 2(1-5):255-262 Abstract Only.

D. Banerjee et al. (2003), "Large-quantity free-standing ZnO nanowires,", Applied Physics Letters, vol. 83, No. 10, 2061-2063.

J. Y. Lao et al., (2002 )"Hierarchical ZnO Nanostructures,", Nano Letters, vol. 2, No. 11, 1287-1291.

J.Y. Lao et al., (2003) "ZnO Nanobridges and Nanonails,", Nano Letters, vol. 3, No. 2, 235-238.

Veriansyah, Kim et al. (2008) "Continuous Synthesis of Surface-Modified Zinc Oxide Nanoparticles Using Supercritical Methanol," *Theories and Applications of Chem. Eng.*, vol. 14, No. 2, Proceedings of the 2008 KIChE Fall Meeting, Oct. 2008, 3316, Abstract Only.

Chen L et al., 2013, "Self-assembled single-crystalline ZnO nanostructures," CrystEngComm, 15, 3780.

* cited by examiner

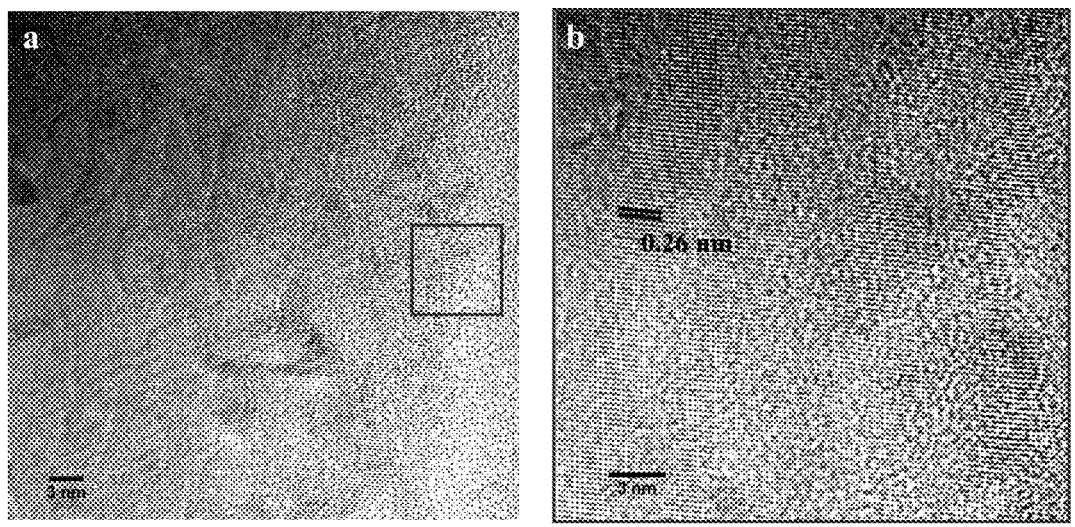
Figs. 6a and b $(\bar{2}110) \wedge (\bar{2}112) = 32.21°$ $(\bar{2}112) \wedge (2\bar{1}\bar{2}) = 64.42°$ ZnO [01$\bar{1}$0]

ZNO STRUCTURES AND METHODS OF USE

CROSS-REFERENCE TO RELATED APPLICATIONS

This application claims the benefit of U.S. Provisional Application No. 61/143,489, filed Jan. 9, 2009, which is hereby incorporated by reference to the extent not inconsistent with the disclosure herein.

BACKGROUND

A major challenge in materials engineering is the controlled assembly of purposefully designed molecules or ensembles of molecules into meso-, micro-, and nanostructures to provide an increasingly precise control at molecular levels over structure, properties and function of materials (Michal, D. W., *Nature* 2000, 405, 293 and Dai, Z. F., et al., *Adv. Mater.* 2001, 13, 1339). The controlled synthesis and characterization of low dimensional crystalline objects is also a major objective in modern materials science, physics and chemistry (Polleux, J., et al., *Angew. Chem. Int. Ed.* 2006, 45, 261 and *Angew. Chem.* 2005, 118, 267). Many researchers have focused on the rational ways to control the shape, size, and dimensionality of nanomaterials. Self-assembly of inorganic nano building blocks into one-dimensional, two-dimensional, and three-dimensional ordered hierarchical nanostructures are fascinating because the variation of the arrangements of the building blocks provides a method to tune the property of the material (Niederberger, M., et al., *J. Am. Chem. Soc.* 2002, 124, 13642; Niederberger, M., et al., *Chem. Mater.* 2002, 14, 4364; Niederberger, M., et al., *Angew. Chem. Int. Ed.* 2004, 43, 2270; Niederberger, M., et al., *J. Am. Chem. Soc.* 2004, 126, 9120; Richards, R., et al., *Angew. Chem. Int. Ed.* 2006, 45, 7277; Richards, R., et al., *J. Phys. Chem. C* 2007, 111, 12038 and Richards, R., et al., *Adv. Mater.* 2008, 20, 267).

ZnO is a particularly interesting oxide as an excellent optoelectronic material because of its wide direct band gap and large exciton binding energy. It has been widely studied as catalyst support for methanol synthesis and decomposition from industrial and experimental processes, because methanol can be used as an alternative energy source to diminish oil and gas resource, as well as a raw material for manmade hydrocarbon and their products (BASF, German Patents, 1923, 415, 686, 441, 443, 462, and 837, U.S. Pat. Nos. 1923, 1,558,559 and 1,569,755; Sun, Q. et al., *J. Catal.* 1997, 167, 92 and Olah, G. A. *Angew. Chem. Int. Ed.* 2005, 44, 2636). ZnO has been proven to be a quite complex and interesting material with a variety of different structures. Therefore many efforts have been exerted to prepare ZnO possessing controlled shapes and morphologies (Yu, H. et al., *J. Am. Chem. Soc.* 2005, 127, 2378; Wu, J. J., et al., *Adv. Mater.* 2002, 14, 215; Tian, Z. R., et al., *J. Am. Chem. Soc.* 2002, 44, 12954 and Zhang, T., et al., *J. Am. Chem. Soc.* 2006, 128, 10960). Various ZnO structures, such as nanocrystals, nanoparticles, nanocubes, nanowires, and nanosheets have been fabricated successfully. Each of these structures can be formed by a different growth mechanism under a wide range of different thermodynamic conditions.

For instance, ZnO nanostructures have been grown directly from a solid source, such as a Zn foil, or using a ZnO film as a nucleation center for the Zn atoms (Yu, H. et al., *J. Am. Chem. Soc.* 2005, 127, 2378). ZnO nanowires have also been grown by vapor deposition methods using metal nanoparticles as a catalyst at high and low temperatures (Wu, J. J., et al., *Adv. Mater.* 2002, 14, 215). Large arrays of oriented helical ZnO nanorods and columns were formed using simple citrate ions to control the growth behavior of the crystal (Tian, Z. R., et al., *J. Am. Chem. Soc.* 2002, 44, 12954). Complex and oriented ZnO nanostructures were synthesized by taking advantage of the preferential adsorption of organic structure-directing agents on different facets of hexagonal ZnO crystals (Zhang, T., et al., *J. Am. Chem. Soc.* 2006, 128, 10960 and Tian Z. R., et al., *Nature Mater.* 2003, 2, 821). The interests in fabricating new ZnO nanostructures have been steadily growing due largely to the exciting new applications (Huang, M. H., et al., *Science* 2001, 292, 1897 and Wang, Z. L., et al., *Science* 2006, 312, 242), which imply the importance of controlling size and shape in ZnO synthesis.

Perfectly ordered oxide surfaces are usually quite inert, so that their chemical and catalytic properties are commonly attributed to the presence of surface defects (Kovacik R., et al., *Angew. Chem. Int. Ed.* 2007, 46, 4894). ZnO is widely used in catalysis, electrical devices, optoelectronics and pharmaceuticals, which often crucially depend on the defect properties of this versatile material. It is becoming increasingly established that in order to control the functional properties of nanoscale materials, it is necessary to control not only their composition, shape and size, but also their defect structure (Spence J. C. H., *Science* 2003, 299, 839). To understand and to control the defect content of inorganic nanostructures can be seen as an important goal (Ischenko V., et al., *Adv. Funct. Mater.* 2005, 15, 1945). However, there is little research about the direct fabrication of ZnO structures which has rich defects, though many efforts have been exerted to prepare ZnO possessing controlled shape and size.

Benzyl alcohol has been found to be a successful medium to tailor metal oxides with well-controlled shape, size and crystallinity under anhydrous conditions, for example, $TiO_2$ nanoparticles of anatase phase in the 4-8 nm size range (Niederberger, M., et al., *Chem. Mate.* 2002, 14, 4364-4370). Vanadium oxide nanorods and tungsten oxide nanoplatelets with identical morphology (Niederberger, M. et al., *J. Am. Chem. So.* 2002, 124, 13642) were synthesized in this medium by Stucky and co-workers from metal chloride precursors. Bimetallic oxides of Perovskite structured $BaTiO_3$, $BaZrO_3$, $LiNbO_3$ (Niederberger, M., et al., *Angew. Chem. In. E.* 2004, 43, 2270) and $SrTiO_3$, $(Ba,Sr)TiO_3$ nanoparticles (Niederberger, M., et al., *J. Am. Chem. So.* 2004, 126, 9120) with controlled particle size and high crystallinity have also been prepared through a suggested C—C bond formation mechanism using metal alkoxides as the starting materials. In all of these studies, no selectivity in surface growth and no nanoscale building rods with rich holes were found. A general drawback of the above sol-gel processes employing benzyl alcohol for tailoring metal oxides with well-controlled shape, size and crystallinity, is the amorphous nature of the derived materials, and the following heat treatment to induce crystallization which usually leads to undesired particle morphology.

SUMMARY

In one aspect, the invention provides ZnO structures comprising crystalline ZnO micro or nanorods, the rods comprising or consisting essentially of characteristic crystallographic features. The ZnO structures of the invention may be used as a catalyst for methanol decomposition and formation at low temperature, dimethyl carbonate formation and photocatalysis. The ZnO structures of the invention may find application in solar cells, fuel cells, electrochemical cells, direct methanol fuel cells (DMFC), electric vehicle propulsion, and in alternative energy technologies, such as hydrogen generation or storage. The inventive ZnO structures may also find application in high density magnetic data storage and as a component or interconnect in nanodevices.

In an embodiment, the surface of the ZnO rods exhibits pits or holes. These pits or holes indicate defects in the crystalline ZnO structures. These pits or holes may contribute to catalytic activity of the ZnO rods. In an embodiment, the diameter or distance spanning the pit is from 1 to 200 nm.

In an embodiment, each ZnO rod has a central region and tip region, with the average width of the tip region being less than that of the central region. The tip region may taper from the central region to the free end of the rod. The rods may have the wurtzite crystal structure. In an embodiment, the surface of the central region is characterized by a set of six crystal facets with an edge region located between each pair of facets. In an embodiment, each central facet corresponds to a crystallographic plane of the form $\{1\ 0\ -1\ 0\}$ $\{0\ 1\ -1\ 0\}$, $\{-1\ 1\ 0\ 0\}$, $\{-1\ 0\ 1\ 0\}$, $\{0\ -1\ 1\ 0\}$ or $\{1\ -1\ 0\ 0\}$ and each central edge region includes a crystallographic plane of the form $\{2\ -1\ -1\ 0\}$ or $\{-2\ 1\ 1\ 0\}$. This central region structure is schematically illustrated in FIGS. 15a and 15b.

In an embodiment, the tip region may also be characterized by a set of six crystal facets with an edge region located between each pair of facets. In an embodiment, each tip facet corresponds to a crystallographic plane of the form $\{1\ 0\ -1\ 1\}$ $\{0\ 1\ -1\ 1\}$, $\{-1\ 1\ 0\ 1\}$, $\{-1\ 0\ 1\ 1\}$, $\{0\ -1\ 1\ 1\}$ $\{1\ -1\ 0\ 1\}$ and each tip edge region includes a crystallographic plane of the form $\{2\ -1\ -1\ 2\}$ or $\{-2\ 1\ 1\ 2\}$. This tip region structure is also schematically illustrated in FIGS. 15a and 15b.

In an embodiment, the invention provides assemblies of ZnO structures having a characteristic "flower-like" morphology, as illustrated in FIGS. 2-3. At least some of the ZnO rods are connected at or near their bases and radiate outward from this connection region. The central portions of these rods have limited contact with each other, so that much of the surface area of the rod is exposed to the environment. The flower-like ZnO structures according to the invention have great commercial and technical potential.

The invention also provides ZnO structures made by the methods of the invention. In an aspect, the invention also provides processes for making the ZnO structures of the invention which are simple, low-cost and practical, and is easy to scale up. In an embodiment, the ZnO structures and structure assemblies are formed via a template-free, halide-free, efficient wet chemical method. Since no templates or surfactants are used, subsequent complicated procedures of removing those substances are not necessary. In an embodiment the ZnO structure are formed from a synthesis mixture which includes a zinc salt precursor material dissolved in an alcohol solvent. In an embodiment, two additives are also present in the synthesis mixture. The first additive may be benzyl alcohol or a substituted benzyl alcohol, while the second additive may be urea or thiourea. In an embodiment, the methods of the invention use a one-pot approach using the inexpensive precursor zinc nitrate, optionally containing water, as a starting material.

Methanol can be used as an alternative energy source to diminishing petroleum resources, as well as a raw material for manmade hydrocarbon and their products and a 'methanol economy' has recently been proposed by Olah as an alternative to a 'hydrogen economy' (Ref. 3c). One of the developments necessary for the realization of a 'methanol economy' is the development of catalysts capable of producing methanol (preferably from $CO_2$) and decomposing methanol into $H_2$ and $CO_2$. Thus, these two reactions have been widely studied in the realms of industry and academics with ZnO supported Cu demonstrating the best results.

In another aspect, the invention provides methods for decomposition of methanol employing the ZnO structures and structure assemblies of the invention. In an embodiment, methanol can be decomposed into carbon monoxide and hydrogen. In another embodiment, methanol can be oxidized to form carbon dioxide. In another embodiment, a mixture of carbon monoxide and carbon dioxide can be formed over the ZnO catalysts of the invention. In an embodiment, methanol decomposition can occur at relatively low temperatures, such as a temperature below 200° C. or 80° C. In an embodiment, the method comprises the step of contacting a zinc oxide microstructure or nanostructure of the invention with a gas including methanol vapor at a temperature from 25° C. to 200° C. for a time from 0.1 h to 12 h. In other embodiments, the temperature may be from 150° C. to 200° C. or 25° C. to 150° C. and the time may be from 0.1 h to 10h.

In another aspect, the invention provides methods for hydrogenation of carbon dioxide, thereby producing methanol. The methods employ ZnO structures and structure assemblies of the invention which are capable of catalyzing hydrogenation of carbon dioxide. In an embodiment, methanol formation can occur at relatively low temperatures, such as a temperature below 200° C. Carbon dioxide hydrogenation is more typically performed with ZnO supported copper catalysts at 220-280° C. (see refs. 3b, 13) so observation of these results for copper-free catalysts is unexpected. In an embodiment, the zinc oxide microstructures or nanostructures are contacted with a gas including carbon dioxide and hydrogen at a temperature from 160° C. to 250° C. for a time from 0.5 h to 20 h.

BRIEF DESCRIPTION OF THE FIGURES

FIG. 6a illustrates a TEM image of a ZnO rod showing the right edge of the material tilted at 2°, and FIG. 6b illustrates a HRTEM image of the ZnO right edge.

DETAILED DESCRIPTION

In one aspect, the invention provides ZnO structures in the form of crystalline "building blocks". These building blocks may be single crystalline. In an embodiment, the building blocks are not simply aggregates of ZnO particles in which separate particles can be distinguished from each other. These building blocks can aggregate to form an assembly of ZnO structures. In an embodiment, the crystal structure of each building block has six-fold symmetry.

As used herein, a material is crystalline if it displays long-range order in the position and stacking sequence of the atoms. A single-crystalline structure displays a characteristic diffraction pattern of regular spots.

Crystallographers can use Miller-Bravais indices to identify the various crystal-facets or crystallographic planes in a hexagonal crystal structure such as wurtzite. The Miller-Bravais index of a crystal plane is defined by the distance and orientation of the plane relative to a set of crystallographic axes and the point of origin.

Figure 15A:
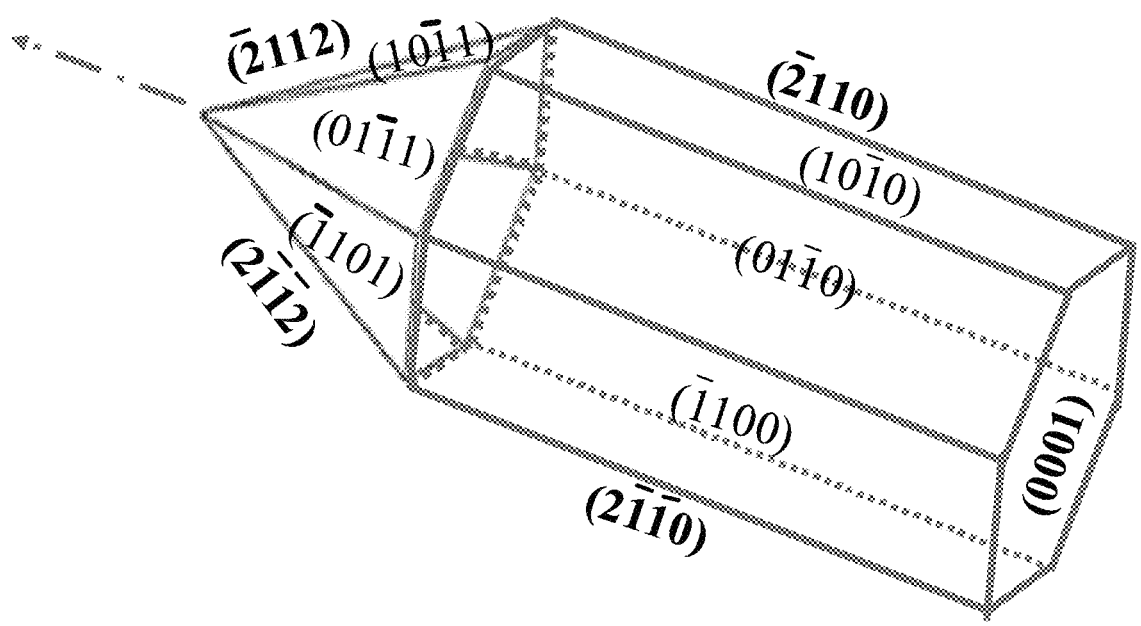
FIGS. 15a and 15b schematically illustrate the ZnO rod geometry, with FIG. 15b being drawn to emphasize the {2 −1 −1 0}, {2 −1 −1 2}, {−2 1 1 2} and {2 −1 −1 2} planes.

FIG. 15a shows a facet labeled (1 0 −1 0) in the central region. This label is the Miller-Bravais index for the plane (1 0 −1 0). According to the art, {1 0 −1 0} designates a family of planes including the (1 0 −1 0), (−1 1 0 0), and (1 0 −1 0) planes.

The vector [1 0 −1 0] points perpendicularly away from the (1 0 −1 0) plane, and <1 0 −1 0> designates a family of vectors including the [1 0 −1 0], [(−1 1 0 0], and [1 0 −1] vectors.

In an embodiment, the ZnO microstructures take the form of crystalline building blocks possessing six-fold symmetry and a wurtzite structure with [0 1 −1 0] orientation (orientation with respect to one of exposed facets). In an embodiment, the building blocks are wurtzite structure with [0 1 −1 0] orientation and the growth direction of the building blocks corresponding to <0001>.

In an embodiment, the six edges of the hexagonal crystal structure have [−2 1 1 0] and [2 −1 −1 0] orientation alternately (orientation with respect to exposed edge regions).

In an embodiment, the ZnO building blocks are elongated and rod-like. In this morphology, the length of the blocks or rods is generally greater than their width. In an embodiment, the blocks are microstructures, having at least one dimension less than one millimeter. In another embodiment, a block or a portion of a block may be a nanostructure, having at least one dimension (e.g. the width) less than 1 micron (micrometer). In an embodiment, a plurality of the blocks or block portions are nanostructures. In an embodiment, the average length of the blocks is in the range 1 to 6 microns. In an embodiment, the average width of blocks (central portion if tapered) is 0.1 to 2 microns. In an embodiment, the average length of the blocks is in the range 2-6 microns, while the average width of the blocks is in the range 1-3 microns. In another embodiment, the length of the blocks is from 1 to 3 microns and the width of the blocks is from 0.1 to 1 micron. In an embodiment, the width at the free end of each block is less than the width in the central portion of the block. In an embodiment, the width of the free end of a block may be less than one micron, so that this end is a nanostructure.

Figure 15B:
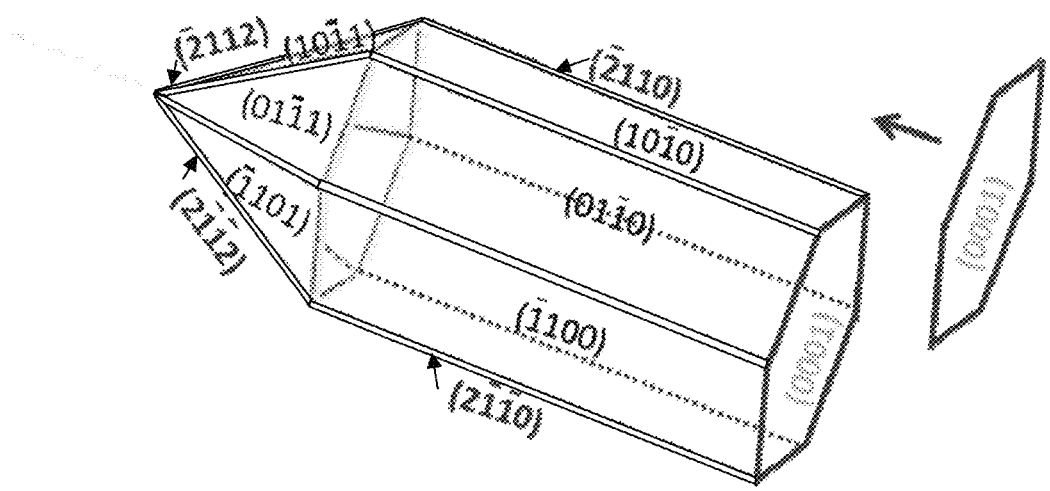

In an embodiment, the block or rod comprises a hexagonal prism central portion and a pyramidal tip, as illustrated schematically in FIGS. 15a and 15b. Without wishing to be bound by any particular belief, the pyramidal tip may contribute to catalytic activity.

In an embodiment, the prisms may be bounded by nonpolar {0 1 −1 0} planes with intersecting edges along {−2 1 1 0} planes while the pyramids are composed of {−1 1 0 1} surfaces with intersecting edges along {−2 1 1 2} planes. Without wishing to be bound by any particular belief, the {−1 1 0 1} surfaces of the pyramids and/or the {−2 1 1 2} edges of the tip may provide catalytic activity for certain reactions.

Figures 2A, 2B, 2C, 2D:
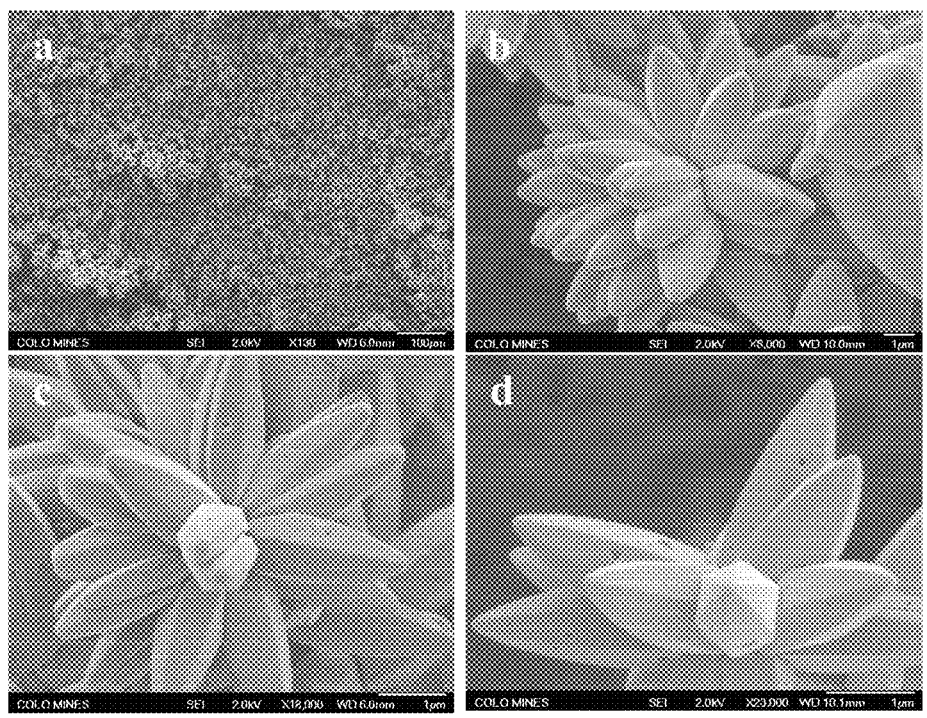
FIG. 2a-2d illustrates field emission scanning electron microscope (FESEM) images of flower-like ZnO structure at different magnifications after calcination.
Figures 3A, 3B:
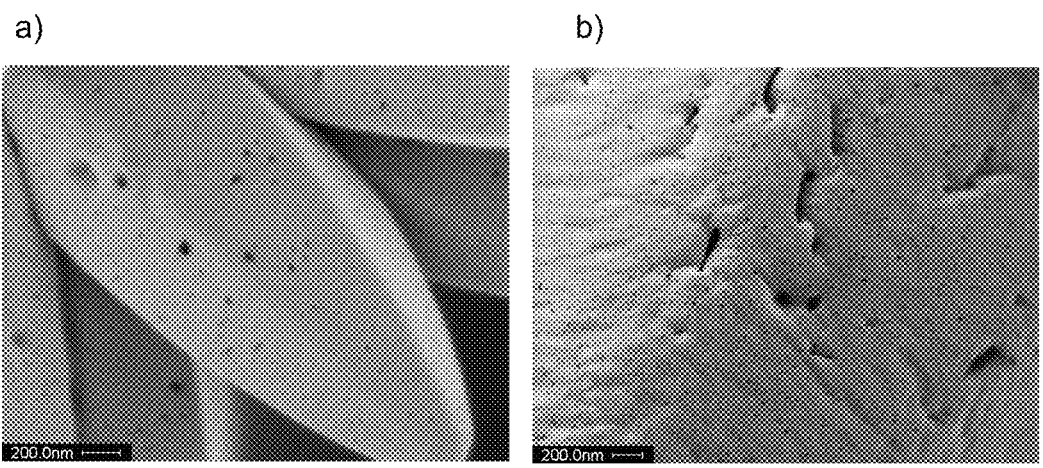
FIGS. 3a and 3b illustrate high magnification SEM images of ZnO rods from aggregated flower-like ZnO structures at different magnification.
Figure 16:
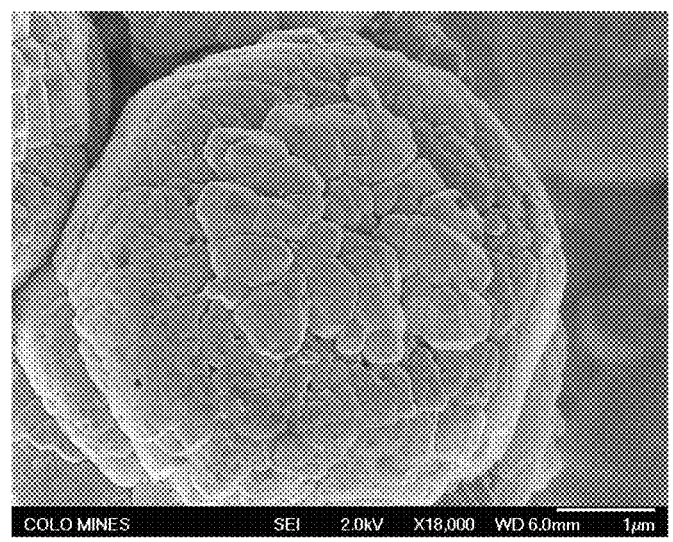
FIG. 16 shows an SEM image of bud-like ZnO structures obtained in the absence of urea.

In an embodiment, the assemblies of blocks or rods look like "blooming flowers" as illustrated in FIGS. 2-3. At least some of the rods are connected at or near their bases and radiate outward from this connection region. The central portions of these rods have limited contact with each other, so that much of the surface area of the rod is exposed to the environment. In an embodiment, the ZnO assemblies have a "flower-like" morphology, each assembly comprising a plurality of ZnO structures, In another embodiment, the assemblies look like "budding" flowers, as illustrated in FIG. 16. In this embodiment, the building blocks are smaller and more closely interconnected.

Figure 1:
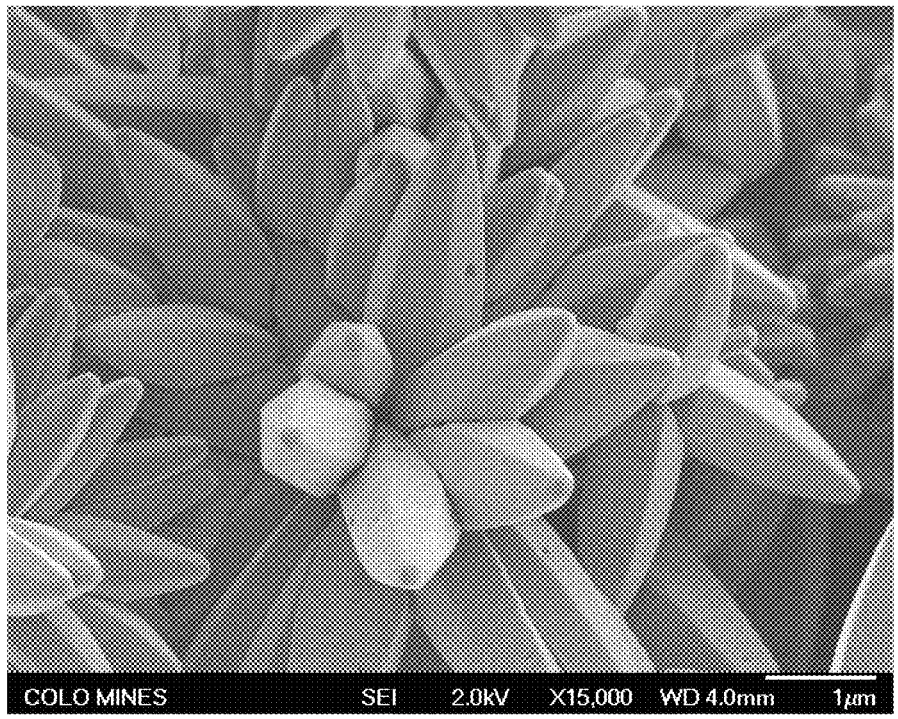
FIG. 1 illustrates scanning electron microscope (SEM) images of flower-like ZnO structure precursor crystals before calcination. The as-synthesized flower-like structure can be seen.

In an embodiment, the flower-like ZnO material according to the invention can be readily identified through a combination of the X-ray diffraction (XRD) pattern and scanning and transmission electron microscopy. In an embodiment, the ZnO material of the invention has the distance of the lattice planes shown in Table 1 in high resolution transmission electron microscopy (HRTEM) when imaging the 6-fold building rod, and has the morphology shown in the scanning electron microscope (SEM) images of FIG. 2a-2d, FIGS. 3a and 3b, FIG. 4a, FIG. 7a, FIG. 8a-8c, FIGS. 9a, 9c and FIG. 10a, the transmission electron microscope (TEM) images of FIG. 4b, FIG. 5a and FIG. 6a, and the high resolution transmission electron microscopy (HRTEM) images of FIG. 4c, FIGS. 5b and 6b, and the powder X-ray diffraction (XRD) pattern of FIG. 11. FIG. 1, which shows the precursor material before calcining, shows similar morphology to the calcined material.

TABLE 1

The index planes of flower-like ZnO structure.

| D observed (Å) | D calculated (Å) | Indexing |
|---|---|---|
| 2.8397 | 2.8143 | 100 |
| 2.6067 | 2.6033 | 002 |
| 2.4725 | 2.4759 | 101 |
| 1.9083 | 1.9111 | 102 |

In an embodiment, the invention provides ZnO structures comprising wurtizite ZnO micro or nanorods, the surface of the ZnO rods exhibiting pits or holes. In different embodiments, the surface area of the ZnO structures is from 0.5 to 5 $m^2/g$, or from 1 to 3 $m^2/g$, as measured with the BET method. In different embodiments, image analysis of the surface of the ZnO structures may show that on average at least 1%, 2%, 5%, 10%, 15% or 25% of the surface includes these pit or hole surface defects. In some regions of the rod, the concentration of these surface defects may be higher.

The side surface of the central portion of the rod may comprise planes of the form $\{1\ 0\ -1\ 0\}$, $\{0\ 1\ -1\ 0\}$, $\{-1\ 1\ 0\ 0\}$, $\{-1\ 0\ 1\ 0\}$, $\{0\ -1\ 1\ 0\}$ or $\{1\ -1\ 0\ 0\}$. The edge regions of the central portion of the rod may include a crystallographic plane of the form $\{2\ -1\ -1\ 0\}$ or $\{-2\ 1\ 1\ 0\}$. The tip of the rod may comprise planes of the form $\{1\ 0\ -1\ 1\}$ $\{0\ 1\ -1\ 1\}$, $\{-1\ 1\ 0\ 1\}$, $\{-1\ 0\ 1\ 1\}$, $\{0\ -1\ 1\ 1\}$ or $\{1\ -1\ 0\ 1\}$. The edge regions of the tip of the rod may include a crystallographic plane of the form $\{2\ -1\ -1\ 2\}$ or $\{-2\ 1\ 1\ 2\}$. Rods may be joined at or near their bases to form the "flower-like" morphology described previously.

In an embodiment, the invention provides methods for making ZnO structures and structure assemblies. In an embodiment, a synthesis mixture is prepared by dissolving a zinc salt in an alcohol solvent, followed by addition of at least two additives.

In an embodiment, the method comprises the steps of:
  a. preparation of a mixture of
    i. zinc salt or a hydrated zinc salt;
    ii. a first additive, wherein the first additive is an alcohol comprising a phenyl group;
    iii. a second additive selected from the group consisting of urea, a urea derivative, thiourea, a thiourea derivative, or combinations thereof;
    iv. an aliphatic alcohol solvent, the aliphatic alcohol having from 1 to 3 carbon atoms;
  b. heating the mixture of step a) from ambient temperature to a first temperature between 180° C. to 200° C. and maintaining the mixture at the first temperature for a time from 1 to 12 h;
  c. heating the mixture of step b) to a second temperature from 240° C. to 300° C. and maintaining the mixture at the second temperature for a time from 1 to 12 h;
  d. removal of the alcohol solvent from the mixture of step c) and
  e. calcination in air of the mixture of step d).

In an embodiment, the zinc salt is selected from the group consisting of zinc nitrate, zinc acetate, zinc citrate, zinc methacrylate, zinc sulfate and zinc oxalate, hydrated forms thereof or combinations thereof. In an embodiment, the zinc salt is zinc nitrate or hydrated zinc nitrate (e.g. zinc nitrate hexahydrate $Zn(NO_3)_2 \cdot 6H_2O$).

In an embodiment, the alcohol solvent is selected so to be capable of dissolving the zinc salt. In an embodiment, the alcohol is an aliphatic alcohol having from 1-3 carbon atoms. In an embodiment, the solvent may be methanol. In an embodiment, the concentration of zinc ions in the solution is from 0.01 mol/l to 1 mol/l.

In an embodiment, the first additive is an alcohol comprising a phenyl group, the first additive being other than a phenol in which the hydroxyl group is directly bonded to the aromatic ring. In an embodiment, the first additive is benzyl alcohol (BA) or a 4-substituted benzyl alcohol or a mixture thereof. In an embodiment, the 4-substituted benzyl alcohol is 4-methoxy benzyl alcohol (MBA). In another embodiment, the 4-substituted benzyl alcohol is 4-nitrobenzyl alcohol (NBA). The first additive may assist in controlling the morphology of the ZnO structures. In embodiment, the ratio of BA and/or substituted BA to Zn is at least two. In different embodiments, the ratio of BA and/or substituted BA to Zn is 2 to 6, 2 to 5, 2 to 4, or 2 to 3.

In an embodiment, the second additive is urea or a urea derivative (having the functional group RR'N—CO—NRR') or a urea or a thiourea derivative (having the functional group RR'N—CS—NRR'). In an embodiment, the second additive is the compound urea $(NH_2)_2CO$. In an embodiment, the second additive can serve the function of producing hydroxide ions. In different embodiments, the ratio of urea to Zn is from 0.1 to 1.0 or from 0.25 to 0.5. In embodiment, the ratio of BA and/or substituted BA to Zn is at least two and the ratio of urea to Zn is from 0.25 to 0.5

Typically, the synthesis mixture will be maintained at a temperature higher than ambient temperature. The synthesis mixture may be maintained at a temperature higher than the boiling temperature of the solution in a closed reaction vessel. In an embodiment, the mixture is maintained at a temperature from 150° C. to 300° C. for a time from 2 to 24 hours. In another embodiment, the mixture is heated from ambient temperature to a first temperature from 180° C. to 200° C. over a time from 1 to 12 h and then maintained at the first temperature for a time from 1 to 12. The mixture may then be heated to a second temperature from 240° C. to 300° C. over a time from 1 to 12 h and the mixture maintained at the second temperature for time from 1 to 12 h.

When the synthesis mixture is placed in a closed reaction vessel, the pressure in the vessel may be greater than one atmosphere. In an embodiment, the pressure in the vessel may be from 6000 torr to 10000 torr.

In an embodiment, the pressure in the reaction vessel is sufficiently high that the critical temperature and pressure of the solvent is exceeded, causing it to enter the supercritical state. The supercritical temperature and pressure depends on the solvent. For methanol, the critical temperature is 512.6 K and the critical pressure is 8.09 MPa; for ethanol the critical temperature is 513.9 K and the critical pressure is 6.14 MPa; for propyl alcohol the critical temperature is 526.5 K and the critical pressure is 5.1 MPa (Eckert C et al., Nature 1996 383, 313).

In an embodiment, no substrate is required for ZnO structure formation. However, in other embodiments, the structures may be grown on a substrate capable of withstanding the synthesis process conditions. The substrate may be glass or quartz or may be selected to provide a particular surface orientation, such as a wafer of known crystal orientation, thereby influencing the growth of the ZnO nanostructures.

In an embodiment, solvent removal is accomplished by a supercritical treatment or drying. In an embodiment the solvent is placed in the supercritical state in a closed reaction vessel, then solvent may be vented from the vessel The mixture may be cooled to ambient temperature before the particles are collected. In an embodiment, the mixture is free cooled, so that cooling is not accelerated. In an embodiment, the free cooling process can take from 1 to 5 h to reach ambient temperature.

In an embodiment, following solvent removal, zinc oxide is formed. In another embodiment, the invention provides the intermediate product of the above synthesis, a flower-like ZnO structure precursor, having the crystalline nature of the desired particle morphology before calcination. An exemplary flower-like ZnO structure precursor before calcination has the scanning electron microscope (SEM) images of FIG. 1 and the crystalline nature of the desired particle morphology before calcination. Without wishing to be bound by any particular belief, the high crystallinity of this intermediate is believed to allow the calcined ZnO to maintain the flower-like structure of the as-synthesized organic-inorganic crystals of the ZnO precursor (before calcination).

Calcination may take place in air. In an embodiment, the calcination temperature is from 400° C. to 600° C. In an embodiment, the calcination ramp rate is from 3 to 10° C./min.

The invention also provides methods for decomposing methanol in which zinc oxide structures of the invention are contacted with a gas including methanol vapor at ambient temperature or above. In an embodiment, the gas supplied to the zinc oxide structures is a mixture of methanol and a carrier gas. Suitable carrier gases include, but are not limited to nitrogen, argon or helium. The gas mixture may also include oxygen. The initial gas concentrations may be expressed in molar percentages or ratios. In an embodiment, the initial concentration of methanol in the gas mixture is from 5% to 30%. In an embodiment, the initial concentration of oxygen in the gas mixture is from 0.001% to 0.5%.

The invention also provides methods for hydrogenating carbon dioxide in which zinc oxide structures of the invention are contacted with a gas including carbon dioxide and hydrogen at greater than ambient temperature. In an embodiment, the gas supplied to the zinc oxide structures is a mixture of carbon dioxide, hydrogen and a carrier gas. Suitable carrier gases include, but are not limited to nitrogen, argon or helium. The gas mixture may also include carbon monoxide. In different embodiments, the initial concentration of carbon dioxide in the gas mixture is from 5 to 30% or from 20% to 30%. In different embodiments, the ratio of hydrogen to carbon dioxide is from 4:1 to 2.5:1 or about 3:1. In an embodiment, the initial concentration of carbon monoxide in the gas mixture is from 0% to 20%.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, and synthetic methods, other than those specifically exemplified can be employed in the practice of the invention without resort to undue experimentation. All art-known functional equivalents, of any such methods, device elements, starting materials, and synthetic methods, are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

In general the terms and phrases used herein have their art-recognized meaning, which can be found by reference to standard texts, journal references and contexts known to those skilled in the art. The preceding definitions are provided to clarify their specific use in the context of the invention.

Example 1

Preparation and Characterization of ZnO Structures

Experimental Details Chemicals: $Zn(NO_3)_2 \cdot 6H_2O$ (98%), urea (98%), anhydrous benzyl alcohol (99.8%), and anhydrous methanol (99.8%) were obtained from Sigma-Aldrich Chemical Incorporation and used without further purification. NanoActive ZnO was received from NanoScale Corporation. The high purity $N_2$ and the mixture of $O_2$ and $N_2$ (20.5% $O_2$ and 79.5% $N_2$) were supplied by General Air Service & Supply, USA.

Preparation of Flowerlike Single Crystalline ZnO: In a Typical preparation, 18g of $Zn(NO_3)_2 \cdot 6H_2O$ was dissolved in 200 ml absolute methanol. After the $Zn(NO_3)_2 \cdot 6H_2O$ totally dissolved, 1.8 g urea and 13 g benzyl alcohol was added to the mixture in the ratio $Zn(NO_3)_2 \cdot 6H_2O$:urea:benzyl alcohol=1:0.5:2 (molar ratio). After stirring for 1 h, the mixture solution was transferred to an autoclave and the reaction mixture was purged with 7500 torr Ar 5 times, and then a pressure of 7500 torr Ar was imposed before initiating heating. The mixture was heated to 200° C. for 5 h, then to 265° C. and maintained at that temperature for 1.5 h; finally, the vapor inside was vented (thereby removing the solvent in the supercritical state). A dry grey powder was collected and subsequently calcined with a ramp rate of 3° C./min to 500° C., then maintained at 500° C. for 6 h. The powder produced from this preparation contains flower-like ZnO structure possessing 6-fold building blocks and wurtzite structure with [01$\bar{1}$0] orientation. The diameters of these 6-fold building blocks are ca. 1-3 µm, and the lengths are ca. 2-6 µm.

As another example, 18g of $Zn(NO_3)_2 \cdot 6H_2O$ was dissolved in 200 ml absolute methanol. After the $Zn(NO_3)_2 \cdot 6H_2O$ totally dissolved, 0.9 g urea and 13 g benzyl alcohol was added to the mixture in the ratio Zn:urea:BA=1:0.25:2 (molar ratio). After stirring for 1 h, the mixture solution was transferred to an autoclave. The autoclave containing the reaction mixture was purged with 10 bar (7500 torr) Ar 5 times, and then a pressure of 10 bar (7500 torr) Ar was imposed before heating starts. The mixture was heated to 200° C. for 5 h, then heated to 265° C. and maintained at that temperature for 1.5 h, at last, the vapour inside was vented. A dry grey powder was collected and subsequently calcined with a ramp rate of 3° C./min to 500° C., then maintained at 500° C. for 6 h. The powder produced from this preparation contains numerous flower-like aggregates of holes rich ZnO structures. The diameters of these 6-fold building blocks are ca. 0.2-1 µm, and the lengths are ca. 1-3 µm.

In another example, 18 g of $Zn(NO_3)_2 \cdot 6H_2O$ was dissolved in 200 ml absolute methanol. After the $Zn(NO_3)_2 \cdot 6H_2O$ dissolved completely, 1.8 g urea was added to the mixture in the ratio Zn:urea=1:2 (molar ratio). After stirring for 1 h, the solution was transferred to an autoclave and the reaction mixture was purged with 7500 torr Ar 5 times, and then a pressure of 7500 torr Ar was imposed before initiating heating. The mixture was heated to 200° C. for 5 h, then to 265° C. and maintained at that temperature for 1.5 h; finally, the vapor inside was vented. After the supercritical fluid drying (SCFD), a green powder was collected and subsequently calcined with a ramp rate of 3° C./min to 500° C., then maintained at 500° C. for 6 h. The powder produced from this preparation contains numerous 6-fold building rods or prisms aggregates of holes rich ZnO structures. The aggregates were flower-like, but less "open" than the flower-like aggregates of the previous two examples. The typical diameter of these building rods or prisms is about 0.3-6 µm, and the lengths of the rods or prisms are about 0.3-2 µm.

Preparation of flower-bud ZnO aggregates 18 g of $Zn(NO_3)_2 \cdot 6H_2O$ was dissolved in 200 ml absolute methanol. After the $Zn(NO_3)_2 \cdot 6H_2O$ dissolved completely, 13 g benzyl alcohol was added to the mixture in the ratio Zn:BA=1:2 (molar ratio). After stirring for 1 h, the solution was transferred to an autoclave and the reaction mixture was purged with 7500 torr Ar 5 times, and then a pressure of 7500 torr Ar was imposed before initiating heating. The mixture was heated to 200° C. for 5 h, then to 265° C. and maintained at that temperature for 1.5 h; finally, the vapor inside was vented. After the supercritical fluid drying (SCFD), a grey powder was collected and subsequently calcined in air with a ramp rate of 3° C./min to 500° C., then maintained at 500° C. for 6 h. The powder produced from this preparation contains numerous flower-bud aggregates of holes rich ZnO structures.

Preparation of Layered Column Structures: 18 g of $Zn(NO_3)_2 \cdot 6H_2O$ was dissolved in 200 ml absolute methanol. After the $Zn(NO_3)_2 \cdot 6H_2O$ dissolved completely, 0.9 g urea and 39 g benzyl alcohol was added to the mixture in the ratio Zn:urea:BA=1:0.5:6 (molar ratio). After stirring for 1 h, the solution was transferred to an autoclave and the reaction mixture was purged with 7500 torr Ar 5 times, and then a pressure of 7500 torr Ar was imposed before initiating heating. The mixture was heated to 200° C. for 5 h, then to 265° C. and maintained at that temperature for 1.5 h; finally, the vapor inside was vented. After the supercritical fluid drying (SCFD), a grey powder was collected and subsequently calcined with a ramp rate of 3° C./min to 500° C., then maintained at 500° C. for 6 h. The powder produced from this preparation contains numerous layered columns aggregates of holes rich ZnO structures. The typical diameter of these columns is about 2-6 µm, the thickness of layers is about 50-100 nm, and the lengths of columns are about 1-4 µm.

Instrumentation: The materials were characterized by powder X-ray diffraction (XRD) using a Siemens D500 X-ray diffractometer with nickel filtered Cu K$\alpha$ radiation ($\lambda$=1.5418 Å) at a scanning rate of $0.1° \cdot min^{-1}$ in the 2$\theta$ range of 10-80°.

Field emission scanning electron microscopic characterization of the samples was carried out on a JEOL JSM-7000F. Transmission electron microscopic and electron diffraction characterization of the samples were carried out on a JEM-2010 operated at 200 kV.

Transmission electron microscopic (TEM) characterization of the flower-like ZnO samples was carried out on a JEM-2010 operated at 200 kV. The samples were prepared by spreading an ultrasonicated suspension in ethanol.

$N_2$ adsorption-desorption isotherms were obtained using a Micrometric's ASAP 2020. The samples were degassed at 300° C. in vacuum for more than 4 h prior to the measurement. The specific surface areas were evaluated with the Brunauer-Emmett-Teller (BET) method in the $P/P_0$ range of 0.05-0.35. Pore size distributions were calculated from the adsorption branch of the isotherms with the Barrett-Joyner-Halenda (BJH) method, and pore sizes were obtained from the peak positions of the distribution curves.

Figure 11:
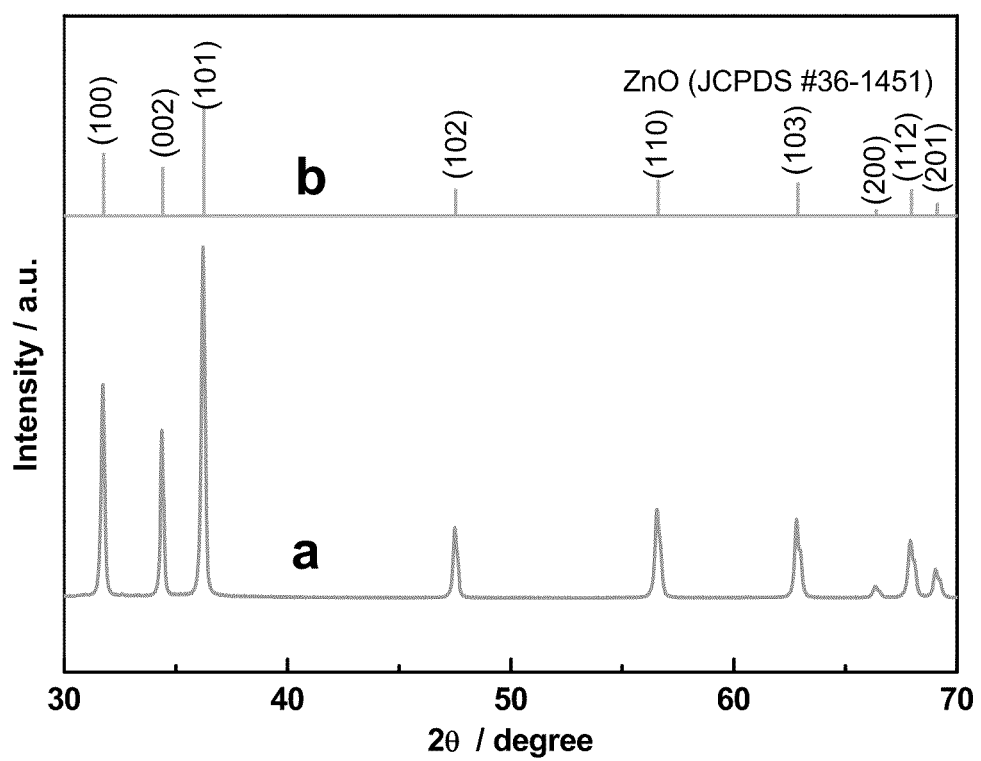
FIG. 11: trace a) illustrates the powder X-ray diffraction (XRD) pattern of flower-like ZnO and trace b) illustrates the standard JCPDS #36-1451 ZnO. The observed lattice spacings are in excellent agreement with wurtzite structure.

FIG. 11, trace a) shows the powder x-ray diffraction (XRD) pattern of the flowerlike ZnO nanostructures calcined at 500° C. The sample was synthesized when these reactants were in the ratio of $Zn(NO_3)_2 \cdot 6H_2O$:urea:benzyl alcohol=1:0.5:2 (molar ratio). The peaks at 2$\theta$=31.7°, 34.4°, 36.3°, 47.5°, 56.6°, 62.8°, 66.4°, 67.9°, 69.1° are observed from FIG. 11 (a). According to standard ZnO XRD pattern (JCPDS card no. 36-1451) shown in FIG. 11 (b), the products are hexagonal ZnO phases (a=0.325 nm, b=0.325 nm, c=0.521 nm), and these peaks are assigned to (100), (002), (101), (102), (110), (103), (200), (112), and (201) diffraction lines of hexagonal ZnO phases, respectively. This indicates that the ZnO is a single phase of well-crystallized ZnO with the hexagonal wurtzite structure (space group: P63mc(186)). The specific surface area measured with the BET technique is ca. 2 $m^2/g$.

Field emission scanning electron microscope (FESEM) images show the morphology of the flower-like ZnO structures before and after calcination at different magnifications.

The as-synthesised product shows a flower-like structure (FIG. 1). After calcination, the ZnO product contains numerous flower-like aggregates (FIGS. 2a-2d). These flowers were composed of 6-fold building blocks, as shown in the FESEM image in FIGS. 2b, 2c and 2d at different magnification. The diameters of these 6-fold building blocks are ca. 1-3 μm, and the lengths are ca. 2-6 μm. It is notable that many hole or pit-like surface features are also observed in these 6-fold building blocks from FIGS. 3a and 3b.

Figures 4A, 4B, 4C:
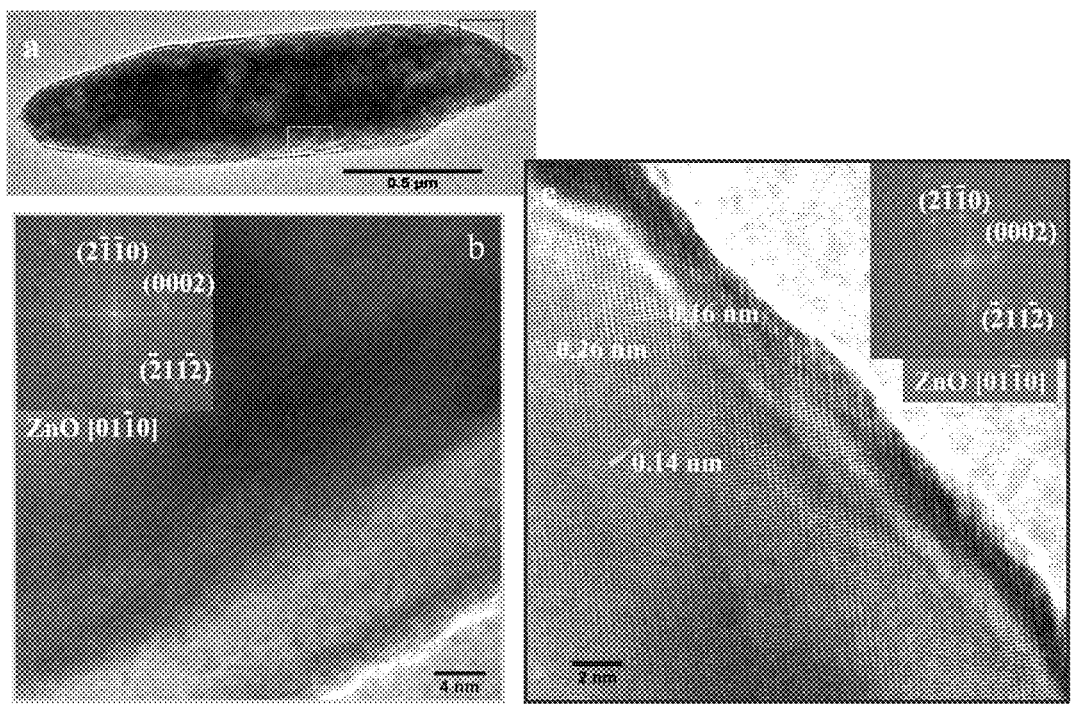
FIG. 4a illustrates a SEM image of a ZnO rod.
FIG. 4b illustrates a selected area TEM image of the ZnO rod and FIG. 4c illustrates a HRTEM image of the ZnO rod. The Fast Fourier Transforms (FFTs), shown in the insets of FIGS. 4b and 4c, reveal that the crystal structure is wurtzite oriented to $Z=[01\bar{1}0]$.
Figures 5A, 5B:
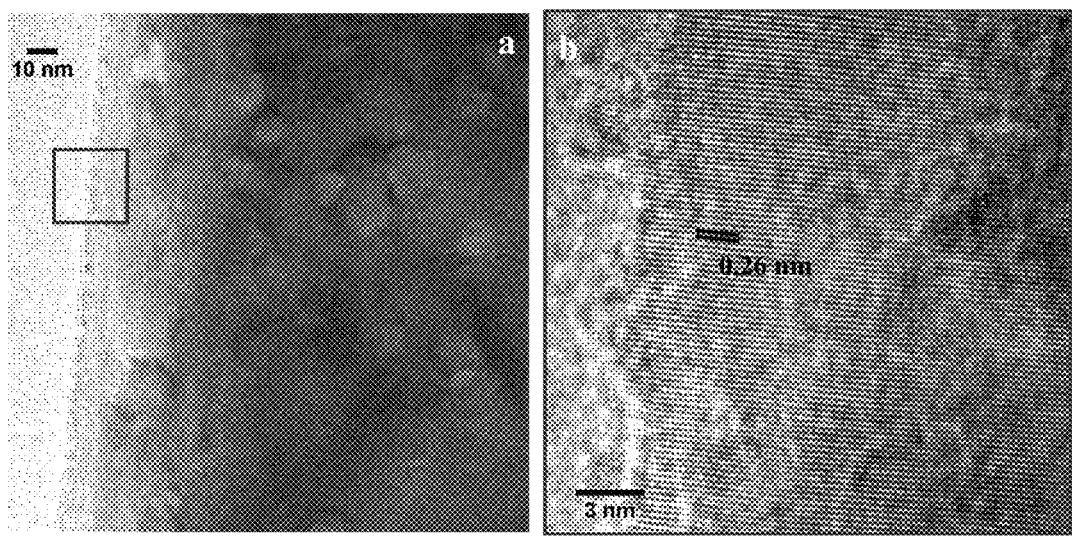
FIG. 5a illustrates a TEM image of a ZnO rod showing the left edge of the material tilted at 2°.
FIG. 5b illustrates a HRTEM image of the ZnO left edge.
Figure 7A:
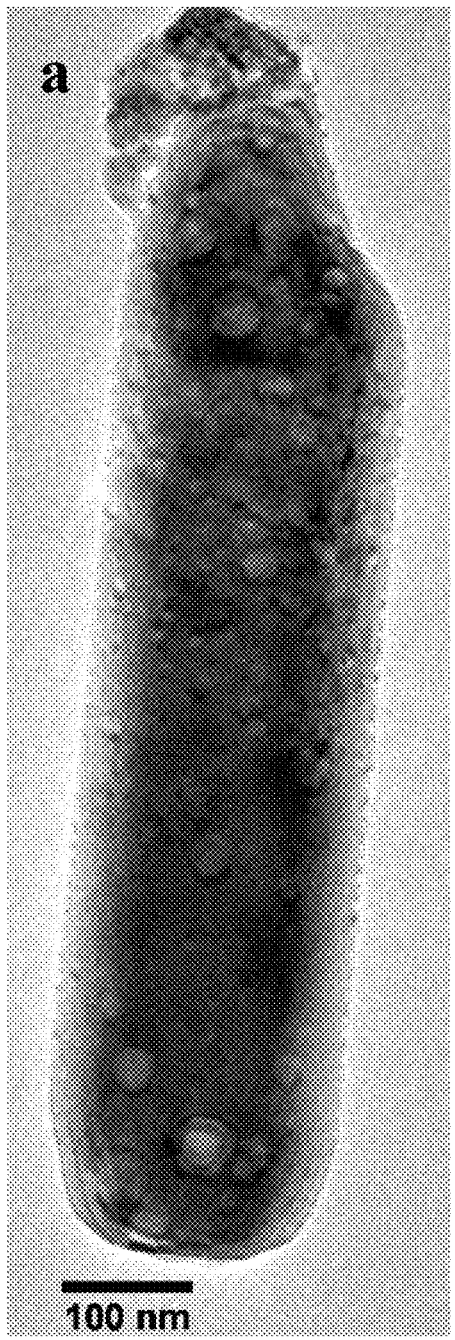
FIG. 7a illustrates a SEM image of a ZnO rod and FIG. 7b illustrates a local selected area electron diffraction pattern of a ZnO rod. The observed SAED shows that the rod presents a hexagonal crystal structure oriented to the $[01\bar{1}0]$ zone axis. The growth direction of the rod corresponds to $\{0001\}$.
Figure 7B:
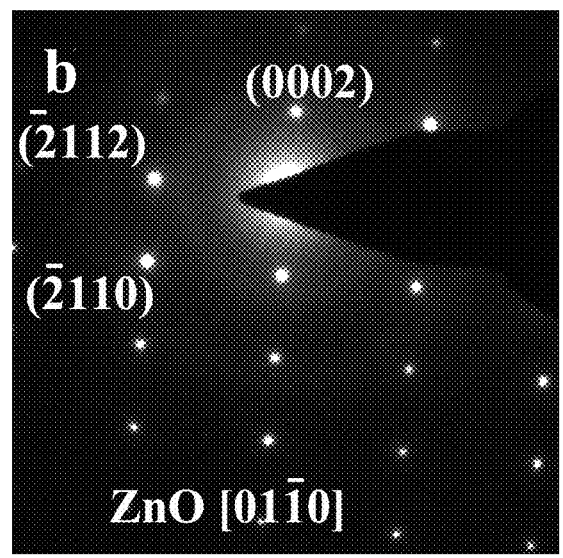
Figures 8A, 8B, 8C, 8D:
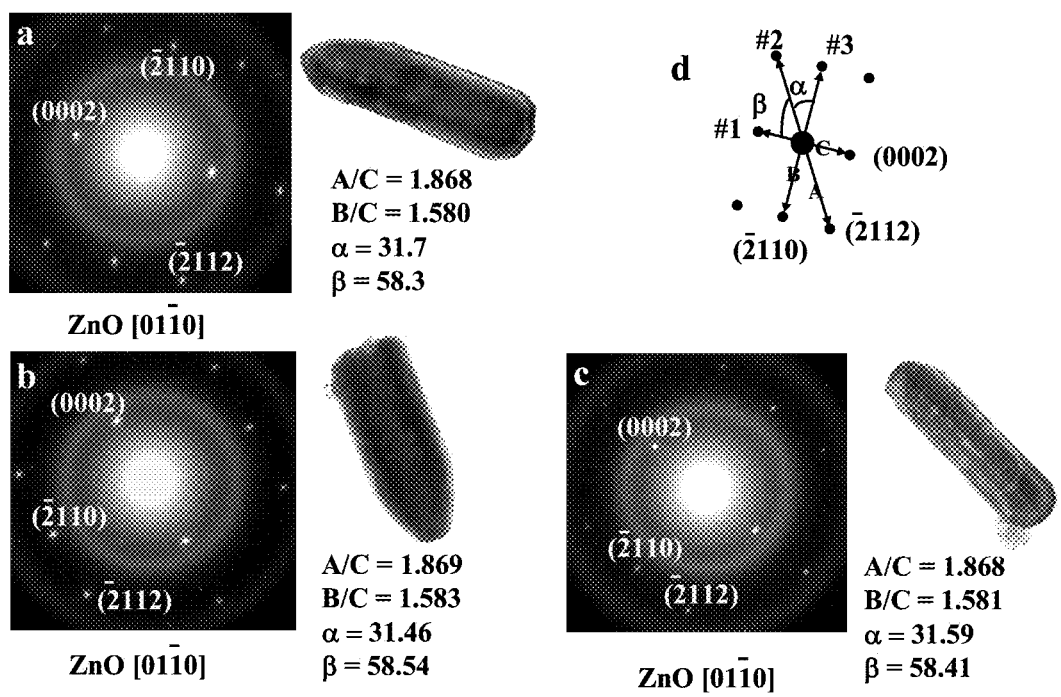
FIGS. 8a-8c illustrate SEM images of ZnO rods and selected area electron diffraction pattern of the ZnO rods. The observed SAED shows that the rods present a hexagonal crystal structure oriented to the $[01\bar{1}0]$ zone axis ($Z=[01\bar{1}0]$). The growth direction of the rod corresponds to $<0001>$.
FIG. 8d is a model of the selected area diffraction pattern.
Figures 9A, 9B:
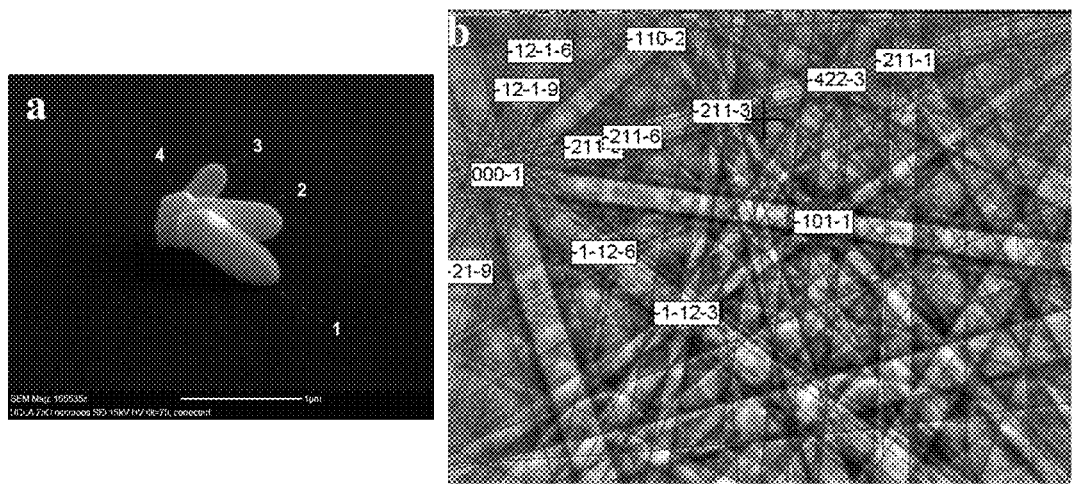
FIG. 9a is an SEM image which illustrates nine different rods analyzed by electron backscatter diffraction (EBSD). All of the rods exhibited the same wurtzite crystal structure.
FIG. 9b illustrates the rod labeled 3 in the adjacent SEM image. The crystal structure is found to be wurtzite, with [01$\bar{1}$0] orientation.
Figure 9C:
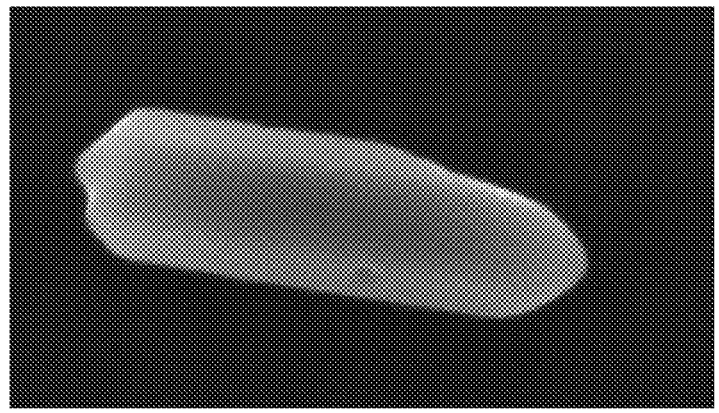
FIG. 9c is another SEM image of a ZnO rod analyzed by EBSD.
Figure 9D:
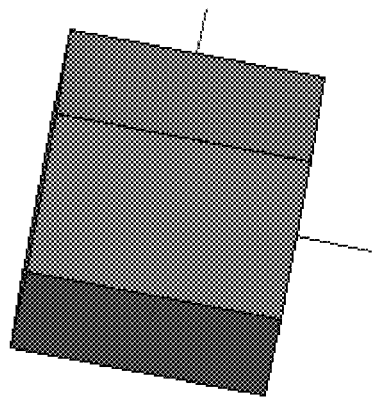
FIGS. 9d and 9e relate to the analysis, with FIG. 9e showing pole figures obtained from the analysis.
Figure 9E:
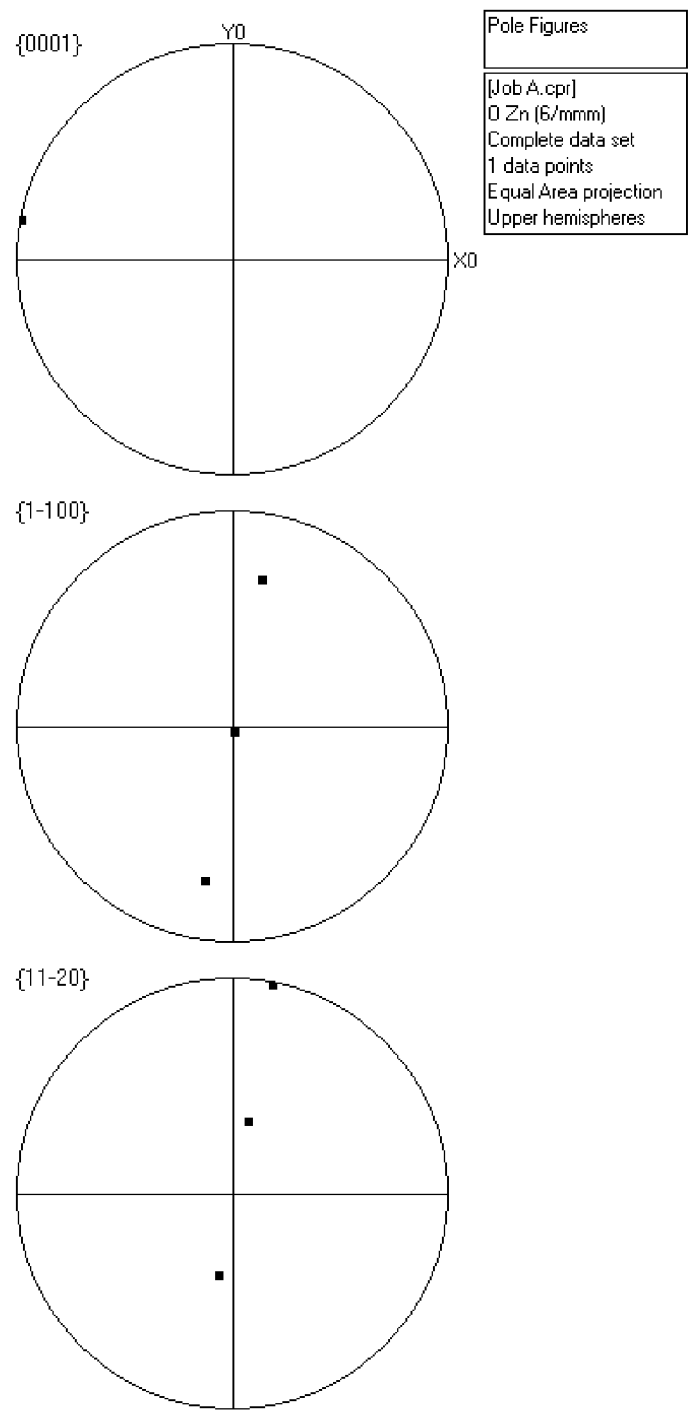
Figure 10A:
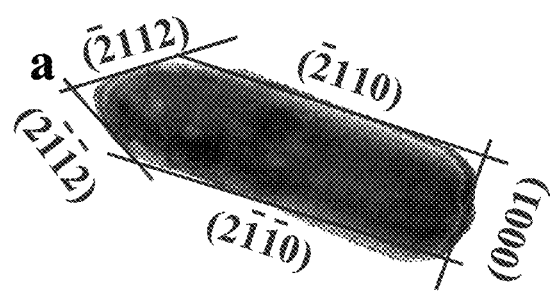
FIGS. 10a and 10b illustrates an SEM image of an individual 6-fold ZnO nano building rod (a), and SAED pattern (b). The edges of the rod tip correspond to (2 −1 −1 2) and (−2 1 1 2) planes. The measured angle results to be 65° close to the theoretical value of 64.42°. The edges along the length are (−2 1 1 0) planes.
Figure 10B:
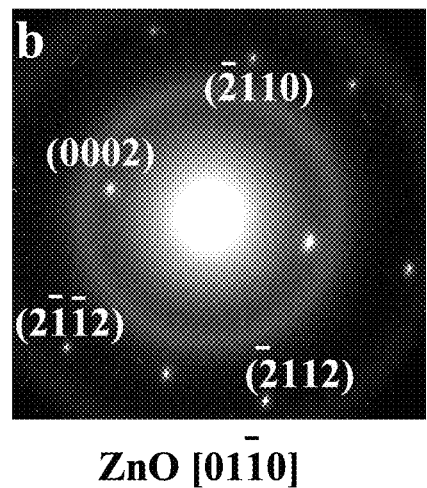

High resolution transmission electron microscope (TEM) images reveal the morphology and structure of these 6-fold building blocks (FIG. 4). FIG. 4a reveals the morphology of one 6-fold building block with holey structure. FIG. 4b shows the TEM of the 6-fold building block. The FFT of selected area can be indexed as the [01$\bar{1}$0] zone axis of single-crystalline ZnO with a hexagonal structure. A representative HRTEM image taken from the 6-fold building block is shown in FIG. 4c. The lattice fringes are clearly visible with a spacing of 0.26, 0.16 and 0.14 nm. The spacing of 0.26 nm corresponds to the lattice fringes of the (0002) planes, the spacing of 0.16 nm corresponds to the lattice fringes of the (2$\bar{1}$$\bar{1}$0) planes, and the spacing of 0.14 nm corresponds to the lattice fringes of the (2$\bar{1}$$\bar{1}$2) planes, respectively. The FFTs (inset) also reveals that the crystal structure is wurtzite oriented to Z=[01$\bar{1}$0]. FIGS. 5a-b and 6a-b show TEM images of a ZnO nanorod of the left and the right edges of the 2°. It indicates the growth direction of the nanorod corresponds to {0001}. Selected Area Electron Diffraction (SAED) (FIG. 7b, FIG. 8a-c) also shows that the nanorod present hexagonal crystal structure oriented to the [01$\bar{1}$0] zone axis. FIG. 9a shows nine different nanorods were analysed by EBSD. All of them exhibited the same wurtzite crystal structure. For example, FIG. 9b is representative raw indexed electron back-scatter pattern (EBSP)s from the nanorod labeled 3 in the adjacent SEM image. The crystal structure is found to be wurtzite, with [01$\bar{1}$0] orientation. We know from the SAED (FIG. 10) that the edges of the nanorod tip correspond to (2$\bar{1}$$\bar{1}$2) and ($\bar{2}$112) planes. The measured angle results to be 65° close to the theoretical value of 64.42°. The edges along the length are ($\bar{2}$110) planes. From the crystal structure, ZnO is wurtzite structure which consists of polar (0001), (000$\bar{1}$) planes and non-polar (1000) planes with C6v symmetry. Due to its anisotropic crystal structure, the c-axis is the most preferred growth orientation, and the velocities of growth in different directions under hydrothermal condition are V[0001]>V[0110]>V[1000] (Wang, M., et al., *J. Cryst. Growth* 2006, 291, 334). The holes indicate the defects in the single-crystalline ZnO structures.

From the SEM images and EBSD data, in combination with TEM images and selected area electron diffraction analyses, the morphology and surface structure of the ZnO flowers were determined as shown in FIG. 15. The images show that the flowers are made up of hexagonal prisms with pyramidal tips. The prisms are bounded by non-polar {01$\bar{1}$0} planes with intersecting edges along {2110} planes while the pyramids are composed of {$\bar{1}$101} surfaces with intersecting edges along {2112} planes. Without wishing to be bound by any particular belief, one explanation for the enhanced catalytic activity observed in these flower structures is the catalytic activity of the {−1101} surfaces of the pyramids and the {2112} edges.

Within this work, several experiments have been carried out to determine the parameters that are important for the formation of ZnO with different shapes and sizes. In the absence of benzyl alcohol and urea, ZnO with the irregular shape were prepared. When the ratio of $Zn(NO_3)_2.6H_2O$:benzyl alcohol=1:2 (molar ratio) is a constant, the size of ZnO 6-fold building rods decreases with decreasing the amount of urea. Smaller ZnO 6-fold building rods with diameter ca. 1 μm were obtained when the ratio of $Zn(NO_3)_2.6H_2O$:urea=1:0.25, the aggregates still look like 'blooming flowers'. In the absence of urea, the length and diameter of ZnO 6-fold building rods decreases considerably, and the aggregates of these smaller ZnO 6-fold building rods look like 'budding flowers' as shown in FIG. 16. According to the experimental results, the role of urea is important to control the size of the ZnO 6-fold building rods and the shape of aggregates in the synthesis method as it provides a steady $OH^-$ supply via urea hydrolysis (Ref. 7). When $Zn(NO_3)_2.6H_2O$ reacts with methanol and water to form the ZnO precursor, acid is a by-product, and the accumulation of acid will inhibit the further formation of the ZnO precursor. However, when urea is added, the $OH^-$ formed by urea hydrolysis neutralizes the acid and allows the formation of the ZnO precursor. Thus, in the self-assembly process, we suggest that the steady $OH^-$ supply controls the size of ZnO building rods by moderating the hydrolysis and alcoholysis rates of zinc nitrate.

Here, benzyl alcohol is used as a structure-directing agent to control the synthesis of ZnO structures. The effect of benzyl alcohol was also investigated. In the absence of benzyl alcohol, although 6-fold building rods or prisms were obtained; the length and diameter are inhomogeneous. Layered columns were formed when the molar ratio of $Zn(NO_3)_2.6H_2O$:urea:benzyl alcohol=1:0.5:6. Thus, since all other parameters were unchanged, it can be inferred that benzyl alcohol plays a critical role as a structure-directing agent to control the shape of these 6-fold building rods. In previous literature, most theories regarding the role of organic compounds are that the organic compounds act as a) simple physical compartments, b) to control nucleation or c) to terminate crystal growth by surface poisoning through selective adsorption on certain planes (See Refs. 4d, 4e, 8). In this case, large amounts of benzyl alcohol lead to decreasing length of 6-fold ZnO rods, and forms these layered ZnO columns and infers that benzyl alcohol may adsorb on (002) planes to terminate the crystal growth. There are many holes in all these ZnO samples (as observed in electron microscopy images) prepared by different methods, and Wang and coworkers. reported the preparation of ZnO rings from ZnO disks; they thought that the formation of a hole could be due to a high density of defects at the center of the ZnO disks that resulted in a high local reaction/etching rate under heating (See Ref. 9). In the case of the present work, a similar hole formation mechanism may occur. The high reaction/etching rate at the defect sites in the ZnO rods may lead to the formation of holes. XRD results showed that all ZnO samples are single phase of well-crystallized ZnO with the hexagonal wurtzite structure.

Example 2

Methanol Dissociation and Carbon Dioxide Hydrogenation

In-situ DRIFTS investigation: A Thermo 6700 IR spectrometer with liquid nitrogen cooled detector, a high temperature environmental chamber and DRIFT accessory were used with the following parameters: 64 scans, 600-4000 $cm^{-1}$ scan range, 4 $cm^{-1}$ resolution.

In-situ DRIFTS investigation of methanol adsorption and surface reaction: The sample temperature was measured through a thermocouple inserted into the sample holder directly in contact with the sample. 10 mg of sample was placed into a high temperature environmental sample holder;

the chamber was heated to 500° C. under nitrogen flow and kept for 2 hours, then the temperature was decreased to room temperature. A spectrum of the ZnO sample was collected at room temperature under nitrogen and was used as the background. Then the sample was exposed to methanol vapor for 2 min by nitrogen at a flow rate of 100 ml per min. The spectra were collected under nitrogen at room temperature. Following this scan, the temperature was raised to 70° C., and another scan was taken, and kept at 70° C. for half an hour, another scan was taken. After this scan, oxygen was introduced at 70° C. and maintained for half an hour, finally, the last spectra was collected at 5 min and half an hour, respectively.

In-situ DRIFTS investigation of $CO_2$ hydrogenation: 10 mg of sample was placed into a high temperature sample holder; the chamber was heated to 500° C. under nitrogen flow and kept for 2 hours, then the temperature was decreased to 180° C. A spectrum of the ZnO sample was collected at 180° C. under nitrogen and was used as the background. Then the mixture of $CO_2$ and $H_2$ (molar ratio of $CO_2$ and $H_2$ is 1:3) was introduced into the chamber at 1 atm, the spectra were collected at different time intervals.

Figure 12:
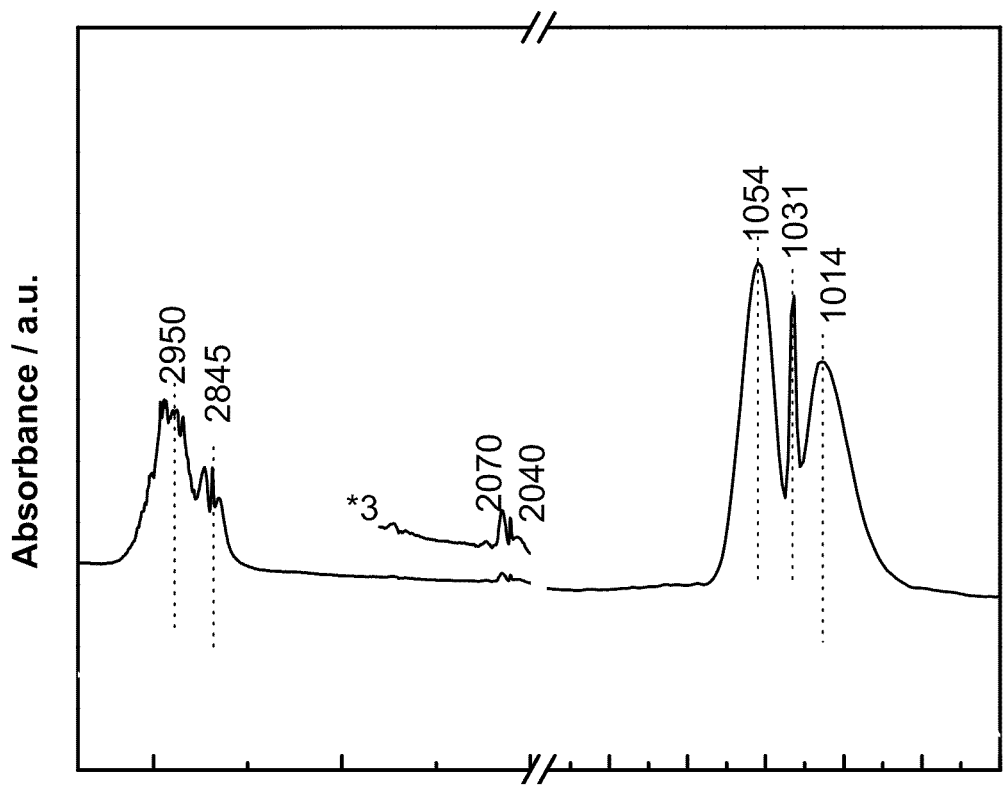
FIG. 12 illustrates a DRIFT spectrum obtained after exposing the flowerlike single crystalline ZnO to methanol vapor introduced $N_2$ flow at room temperature for 2 min.
Figure 13:
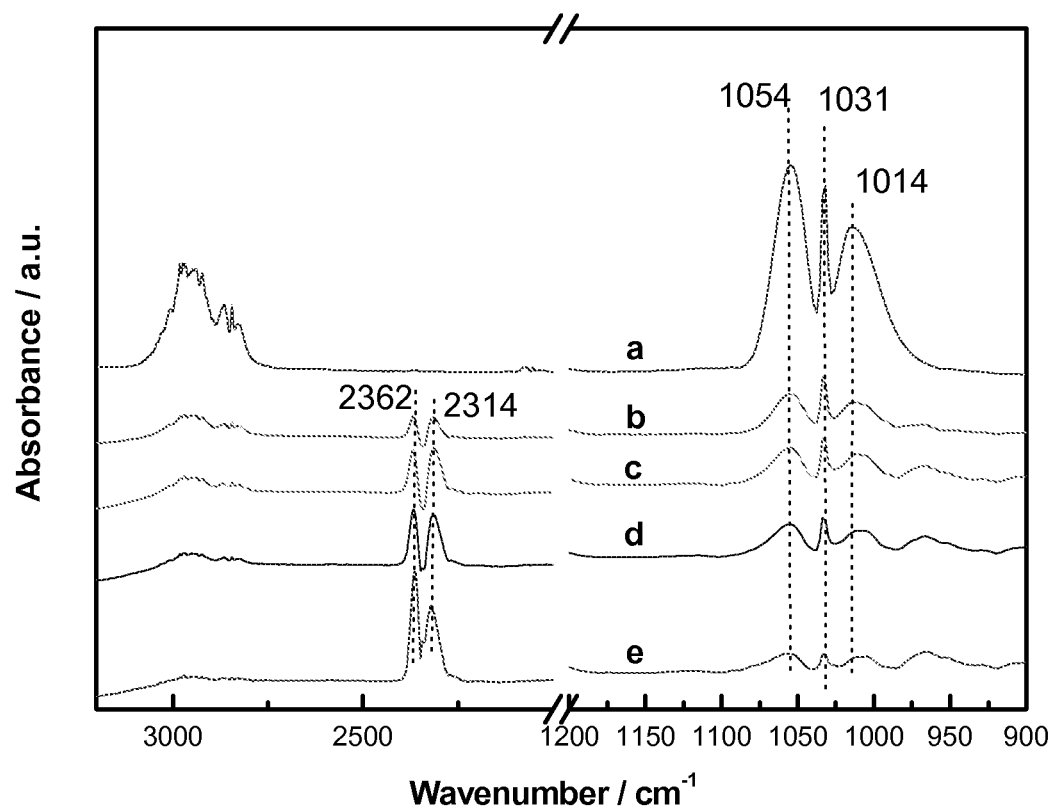
FIG. 13 illustrates DRIFT spectra obtained after exposing the flowerlike single crystalline ZnO to methanol vapor introduced $N_2$ flow at room temperature for 2 min (a), heated to 70° C. (b), kept at 70° C. for 30 min (c), oxygen introduced and kept for 5 min at 70° C. (d), and oxygen introduced and kept for 30 min at 70° C. (e).

Defects at metal oxide surfaces are thought to significantly influence a variety of surface properties, including chemical reactivity (Li, F., et al., *Angew. Chem. Int. Ed.* 2004, 43, 5238). Methanol is a 'smart' molecular probe that can provide fundamental information about the number and the nature of active surface sites (BASF., German Patents, 1923, 415, 686, 441, 443, 462, and 837, U.S. Pat. Nos. 1,558,559 and 1,569, 755; 1923, Sun, Q., et al., *J. Catal.* 1997, 167, 92 and Olah, G. A. *Angew. Chem. Int. Ed.* 2005, 44, 2636). Methanol decomposition has been found to be structure sensitive, in that the selectivity depends on the arrangement of the surface atoms. Methanol also can be an interesting combustible for fuel cells. We investigated methanol adsorption and reaction on the surface of ZnO structures by diffuse reflectance infrared Fourier transform (DRIFT) spectroscopic techniques at low temperatures. DRIFT spectra of the flowerlike single crystalline ZnO exposed to methanol vapor introduced by nitrogen flow at room temperature was collected (FIG. 12). At room temperature, methanol interacts molecularly and dissociatively with flowerlike single crystalline ZnO. The molecular interactions are indicated by the C—O stretching peak centered at 1031 $cm^{-1}$ and the corresponding symmetric and asymmetric C—H stretching contributions at 2845 and 2950 $cm^{-1}$. The dissociative interactions are indicated by the C—O stretching region 1054 and 1014 $cm^{-1}$, and the presence of methoxyl groups is confirmed by the signals corresponding to the symmetric and asymmetric C—H stretching centered at 2819 and 2922 $cm^{-1}$ (Natile, M. M., et al., *Chem. Mater.* 2006, 18, 3270 and Natile, M. M., et al., *Chem. Mater.* 2005, 17, 3403). It is worth noting that carbon monoxide as indicated by the peaks at 2070 and 2040 $cm^{-1}$ was observed on the surface of flowerlike single crystalline ZnO. This indicated that methanol can be oxidized into carbon monoxide in absence of oxygen on the surface of flowerlike single crystalline ZnO at room temperature. Methanol dissociation and oxidation on the surface of flowerlike single crystalline ZnO is favored by the increasing temperature. When the temperature was increased to 70° C. under nitrogen, methanol was decomposed partly into carbon dioxide as indicated by the peaks at 2362 and 2314 $cm^{-1}$ and carbon monoxide disappeared (FIG. 13b). Methanol was further oxidized a little after it was kept at 70° C. for half an hour (FIG. 13c). When oxygen by a mixture of oxygen and nitrogen (20.5% oxygen and 79.5% nitrogen) was introduced into the in-situ chamber, and kept for 5 min, methanol was further oxidized as indicated by the peaks increasing centered at 2362 and 2314 $cm^{-1}$ and the decreasing of peaks in the C—H stretching region between 2800 and 3000 $cm^{-1}$ and the peaks in the C—O stretching region centered at 1054, 1031 and 1014 $cm^{-1}$ (FIG. 13d). After half an hour, methanol was almost oxidized completely (FIG. 13e).

For comparison, DRIFT spectra were also collected for NanoActive ZnO with high surface area (from NanoScale Corporation, 70 $m^2/g$ and crystallite size≤10 nm) exposed to methanol vapor introduced by nitrogen flow at room temperature. At room temperature, methanol interacted molecularly and dissociatively with the NanoActive ZnO. It is worth noting that peaks at 2070 and 2040 $cm^{-1}$, corresponding to carbon monoxide, were not detected for the room temperature experiment with NanoActive ZnO. In addition, when the same higher temperature experiments described in the previous paragraph were done on the surface of NanoActive ZnO, neither carbon dioxide nor carbon monoxide was observed under nitrogen even at 70° C. for half an hour. After oxygen was introduced, methanol was oxidized and carbon dioxide was observed as indicated by the peaks at 2362 and 2314 $cm^{-1}$. Methanol can be further oxidized partly by oxygen with increasing reaction time on the surface of NanoActive ZnO. After the adsorption and reaction of methanol, the color of flowerlike single crystalline ZnO did not change, but the NanoActive ZnO became black. This indicated that carbon deposited on the surface of NanoActive ZnO, but on the surface of the flowerlike single crystalline ZnO, methanol was completely oxidized into carbon dioxide.

Carbon dioxide has become the focus of attention recently because it is a major greenhouse gas and a cheap C1 resource. The conversion of $CO_2$ into value-added chemicals has also attracted much attention in recent years (Jessop, P. G., et al., *Chem. Rev.* 1995, 95, 259; Leitner, W. *Angew. Chem. Int. Ed.* 1995, 34, 2207; Shaikh, A. A., et al., *Chem. Rev.* 1996, 96, 951; Gibson, D. H. *Chem. Rev.* 1996, 96, 2063 and Yu, K. M. K., et al., *J. Am. Chem. Soc.* 2007, 129, 6360). The hydrogenation of $CO_2$ to produce formic acid or methanol is an attractive reaction system (Jessop, P. G., et al., *Nature* 1994, 368, 231 and Munshi, P., et al., *J. Am. Chem. Soc.* 2002, 124, 7963). $CO_2$ hydrogenation is run mostly on Cu/ZnO catalysts at temperatures of 220-280° C. (BASF., German Patents, 1923, 415, 686, 441, 443, 462, and 837, U.S. Pat. Nos. 1,558, 559 and 1,569,755; 1923, Sun, Q. et al., *J. Catal.* 1997, 167, 92 and Zhang, Z., et al., *Angew. Chem. Int. Ed.* 2008, 47, 1127).

Figure 14:
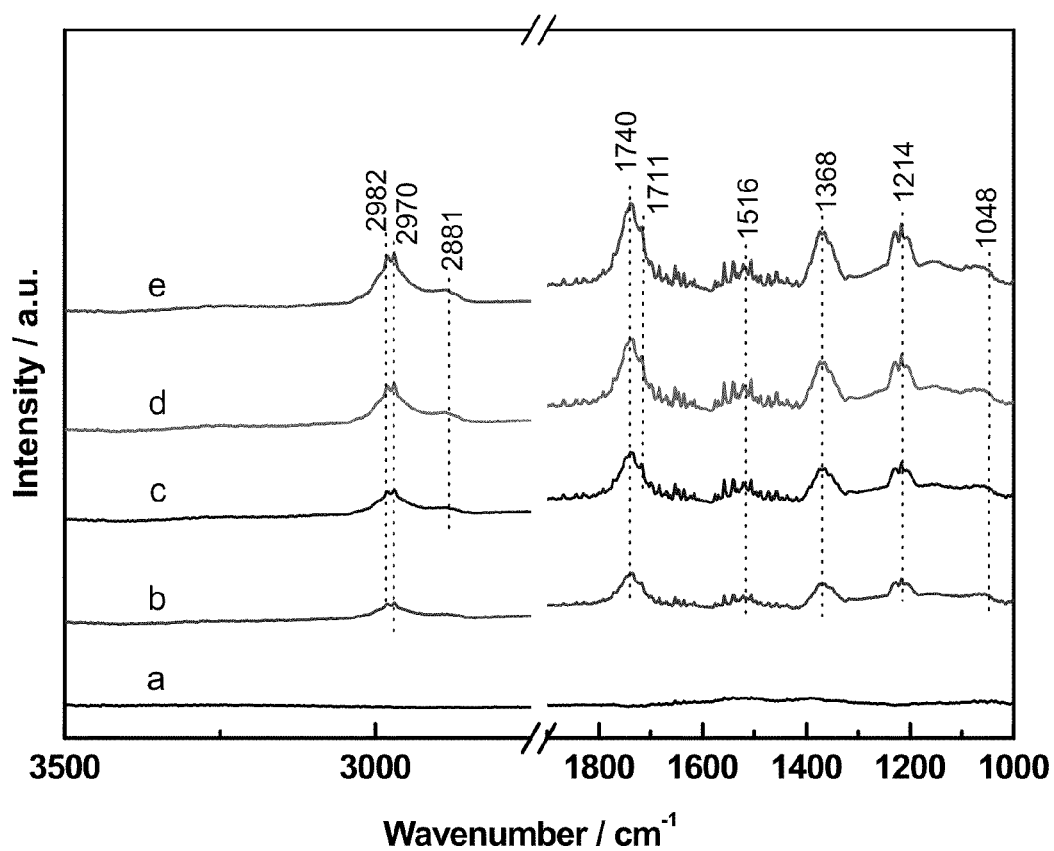
FIG. 14 illustrates DRIFT spectra obtained after exposing the flowerlike single crystalline ZnO to $CO_2$ and $H_2$ at 180° C. for 1 min (a), 10 min (b), 20 min (c), 40 min(d), 60 min (e).

Surprisingly, the Cu-free flowerlike ZnO showed high activity for $CO_2$ hydrogenation as shown in FIG. 14, which shows DRIFT spectra obtained after exposing the flowerlike single crystalline ZnO to $CO_2$ and $H_2$ at 180° C. for 1 min (a), 10 min (b), 20 min (c), 40 min(d), 60 min (e). At 180° C. for 10 min, the C—H stretching bands were observed at 2982, 2970 and 2881 $cm^{-1}$, in the meantime, two types of C=O stretching bands at 1740 and 1711 $cm^{-1}$ which can attributed to adsorbed formate and formaldehyde, respectively; the bands at 1516, 1368, 1214 $cm^{-1}$ which can attribute to adsorbed formic acid and the band at 1048 $cm^{-1}$ which can be attributed to C—O stretching of adsorbed methoxyl group (Schilke, T. C., et al., *J. Catal.* 1999, 184, 144 and Jung, K. D., et al., *J. Catal.* 2000, 193, 207). These results indicate that the products of $CO_2$ hydrogenation include formic acid, formaldehyde and methanol. The strength of these peaks increased with the increasing of reaction time. These results indicate that the flowerlike single crystalline ZnO showed good surface activity. Without wishing to be bound by any particular belief, the surface activity may be due to the presence of large amount of holes (defect sites), the crystallographic orientation at the tip of the ZnO building blocks, or a combination thereof.

For comparison, hydrogenation of $CO_2$ was not observed over NanoActive ZnO with high surface area. Only hydrogen and $CO_2$ adsorption, which are indicated by the peaks in the range of 3500-3900 $cm^{-1}$ and in the range of 1000-1700 $cm^{-1}$, respectively, were observed

We claim:

1. A zinc oxide structure comprising a plurality of microrods or nanorods, each rod exhibiting the wurtzite crystal structure, the longitudinal axis of each rod being aligned with the <0001> direction of the wurtzite crystal structure and each rod including
   a. a central region, the surface of the central region including
      i. six central facets, each central facet corresponding to a crystallographic plane of the form {1 0 –1 0}, {0 1 –1 0}, {–1 1 0 0}, {–1 0 1 0}, {0 –1 1 0} or {1 –1 0 0};
      ii. six central edge regions, each central edge region being located between two central facets and including a crystallographic plane of the form {2 –1 –1 0} or {–2 1 1 0}; and
   b. a tip region connected to the central region, the width of the rod in the tip region being less than that in the central region
   wherein the surface of the central region, the tip region or a combination thereof includes a plurality of pits, the distance spanning each pit being from 1 nm to 200 nm.

2. The zinc oxide structure according to claim 1, wherein the surface of the tip region includes
   i. six tip facets, each tip facet corresponding to a crystallographic plane of the form {1 0 –1 1}, {0 1 –1 1}, {–1 1 0 1}, {–1 0 1 1}, {0 –1 1 1} or {1 –1 0 1}; and
   ii. six tip edge regions, each tip edge region being located between two tip facets and including a crystallographic plane of the form {2 –1 –1 2} or {–2 1 1 2}.

3. The zinc oxide structure according to claim 1, wherein at least 1% of the surface of the zinc oxide structure includes pits.

4. The zinc oxide structure according to claim 1, wherein the length of each rod is from 1 to 6 microns.

5. The zinc oxide structure according to claim 1, wherein the width of the central region of each rod is from 0.1 to 2 microns.

6. The zinc oxide structure according to claim 1, wherein each rod further comprises a base region opposite the tip region, and the base regions of the rods are conjoined.

7. A zinc oxide structure made by a method comprising the steps of
   a. preparation of a mixture of
      i. a zinc salt or a hydrated zinc salt, the zinc salt being selected from the group consisting of zinc nitrate, zinc acetate, zinc citrate, zinc methacrylate, zinc sulfate and zinc oxalate;
      ii. a first additive, the first additive being an alcohol comprising a phenyl group;
      iii. a second additive selected from the group consisting of urea, a urea derivative, thiourea, a thiourea derivative and combinations thereof; and
      iv. an aliphatic alcohol solvent, the aliphatic alcohol having from 1 to 3 carbon atoms;
   b. heating the mixture of step a) to a first temperature from 180° C. to 200° C. and maintaining the mixture at the first temperature for a time from 1 to 12 h;
   c. heating the mixture of step b) to a second temperature from 240° C. to 300° C. and maintaining the mixture at the second temperature for a time from 1 to 12 h;
   d. removal of the alcohol solvent from the mixture of step c) and
   e. calcination in air of the mixture of step d),
   wherein the zinc oxide structure comprises a plurality of microrods or nanorods, each rod exhibiting the wurtzite crystal structure, the longitudinal axis of each rod being aligned with the <0001> direction of the wurtzite crystal structure and each rod including a central region, the surface of the central region including six central facets and six central edge regions, each central edge region being located between two central facets and a tip region connected to the central region, the width of the rod in the tip region being less than that in the central region;
   the surface of the zinc oxide structure including a plurality of pits, the distance spanning each pit being from 1 nm to 200 nm.

8. A method for decomposing methanol, the method comprising the step of:
   contacting the zinc oxide structure according to claim 1 with a gas including methanol vapor at a temperature from 25° C. to 200° C. for a time from 0.1 h to 12 h.

9. The method of claim 8, wherein the methanol is contacted with the zinc oxide structure at a temperature from 25° C. to 150° C. for a time from 0.1 h to 10 h.

10. The method of claim 8, wherein the gas further includes oxygen.

11. A method for hydrogenation of carbon dioxide, the method comprising the step of:
   contacting the zinc oxide structure according to claim 1 with a gas including carbon dioxide and hydrogen at a temperature from 160° C. to 250° C. for a time from 0.5 h to 20 h.

12. The method of claim 11, wherein the ratio of hydrogen to carbon dioxide is from 2.5 to 4.

13. The method of claim 11, wherein the gas further includes carbon monoxide.

14. The method of claim 13, wherein the concentration of carbon monoxide in the gas mixture is greater than 0 and less than or equal to 20%.

15. The zinc oxide structure of claim 1 wherein the tip region tapers from the central region to the free end of the rod.

16. The zinc oxide structure of claim 1 wherein the tip is pyramidal in shape.

17. The zinc oxide structure according to claim 7, wherein at least 1% of the surface of the zinc oxide structure includes pits.

18. The zinc oxide structure according to claim 7, wherein the length of each rod is from 1 to 6 microns.

19. The zinc oxide structure according to claim 7, wherein the width of the central region of each rod is from 0.1 to 2 microns.

20. The zinc oxide structure according to claim 7, wherein each rod further comprises a base region opposite the tip region, and the base regions of the rods are conjoined.

21. The zinc oxide structure of claim 7 wherein the tip region tapers from the central region to the free end of the rod.

22. The zinc oxide structure of claim 7 wherein the tip is pyramidal in shape.

* * * * *